US009527849B2

(12) United States Patent
Li et al.

(10) Patent No.: US 9,527,849 B2
(45) Date of Patent: Dec. 27, 2016

(54) SALT AND POLYMORPH OF PYRAZOLOPYRIMIDINONE COMPOUND, AND PHARMACEUTICAL COMPOSITION CONTAINING THE SAME, PREPARATION METHOD AND USE THEREOF

(75) Inventors: Jianfeng Li, Shanghai (CN); Guanghui Tian, Shanghai (CN); Zhen Wang, Shanghai (CN); Jin Suo, Shanghai (CN); Xiangrui Jiang, Shanghai (CN); Zheng Liu, Shanghai (CN); Xiaojun Yang, Shanghai (CN); Zhu Xie, Shanghai (CN); Xianguo Zhao, Shanghai (CN); Weiliang Zhu, Shanghai (CN); Hualiang Jiang, Shanghai (CN); Jingshan Shen, Shanghai (CN)

(73) Assignees: TOPHARMAN SHANGHAI CO., LTD., Shanghai (CN); SHANGHAI INSTITUTE OF MATERIA MEDICA, CHINESE ACADEMY OF SCIENCES TOPHARMAN SHANDONG CO., LTD, Shanghai (CN)

( * ) Notice: Subject to any disclaimer, the term of this patent is extended or adjusted under 35 U.S.C. 154(b) by 156 days.

(21) Appl. No.: 14/238,790

(22) PCT Filed: Aug. 14, 2012

(86) PCT No.: PCT/CN2012/001082
§ 371 (c)(1),
(2), (4) Date: Jun. 13, 2014

(87) PCT Pub. No.: WO2013/023439
PCT Pub. Date: Feb. 21, 2013

(65) Prior Publication Data
US 2014/0309241 A1    Oct. 16, 2014

(30) Foreign Application Priority Data
Aug. 17, 2011   (CN) .......................... 2011 1 0236585

(51) Int. Cl.
| | | |
|---|---|---|
| *C07D 487/04* | (2006.01) | |
| *A61K 31/519* | (2006.01) | |
| *A61P 15/10* | (2006.01) | |
| *A61P 13/10* | (2006.01) | |
| *A61P 9/10* | (2006.01) | |
| *A61P 9/04* | (2006.01) | |
| *A61P 13/12* | (2006.01) | |
| *A61P 11/06* | (2006.01) | |
| *A61P 29/00* | (2006.01) | |

(Continued)

(52) U.S. Cl.
CPC ......... *C07D 487/04* (2013.01); *C07B 2200/13* (2013.01)

(58) Field of Classification Search
CPC .................................................. C07D 487/04
See application file for complete search history.

(56) References Cited

U.S. PATENT DOCUMENTS 3,832,460 A * 8/1974 Kosti ....................... A61K 8/41
424/54
5,795,909 A * 8/1998 Shashoua ......... A61K 47/48038
514/449

(Continued)

FOREIGN PATENT DOCUMENTS

CN          1325398 A      12/2001
WO       2007056955 A1      5/2007

OTHER PUBLICATIONS

Berge (J. of Pharmaceutical Sciences, 1977, vol. 66(1), pp. 1-19).*

(Continued)

*Primary Examiner* — Susanna Moore
(74) *Attorney, Agent, or Firm* — Quarles & Brady LLP

(57) ABSTRACT

The present invention relates to new salts of pyrazolopyrimidinone represented by formula (I), and pharmaceutically acceptable polymorph, solvate, hydrate, dehydrate, co-crystallization, anhydrous, or amorphous form thereof, the pharmaceutical compositions, and a pharmaceutical unit dosage form containing the same, wherein x represents organic or inorganic acids, preferable maleic acid, succinic acid, methanesulfonic acid, hydrochloric acid, etc. The invention further relates to co-crystals or complexes of compounds of pyrazolopyrimidinone and pharmaceutical compositions containing the same. The present invention also relates to a process for the preparation, use thereof and pharmaceutical preparation containing the salts or crystalline forms.

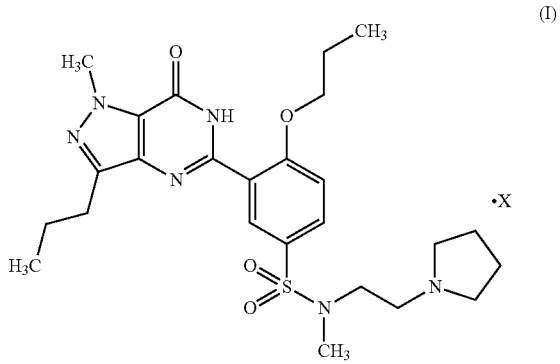

4 Claims, 10 Drawing Sheets

Figure 1:
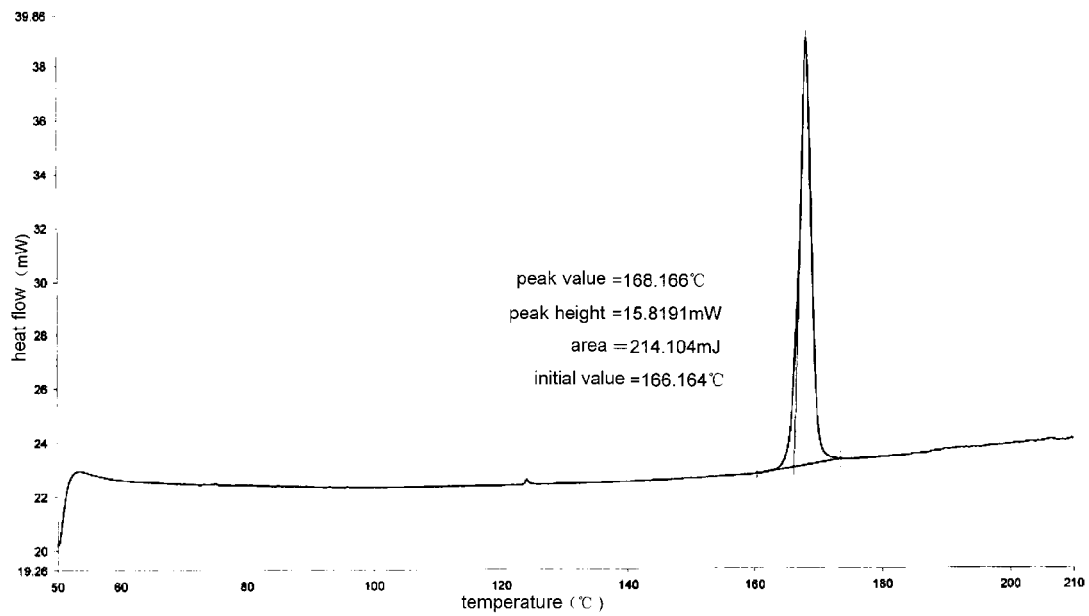

(51) Int. Cl.
  *A61P 27/06* (2006.01)
  *A61P 9/12* (2006.01)

(56) References Cited

U.S. PATENT DOCUMENTS

| | | | |
|---|---|---|---|
| 6,624,138 B1* | 9/2003 | Sung | A61L 27/34 424/422 |
| 7,167,750 B2* | 1/2007 | Knudson | A61N 1/05 607/133 |
| 2006/0223794 A1* | 10/2006 | Bourghol Hickey | A61K 9/145 514/220 |
| 2007/0112039 A1* | 5/2007 | Grant | C07D 213/75 514/352 |
| 2008/0318949 A1* | 12/2008 | Tian | C07D 487/04 514/234.2 |

OTHER PUBLICATIONS

International search report under date of Nov. 7, 2012 in connection with PCT/CN2012/001082.

* cited by examiner

SALT AND POLYMORPH OF PYRAZOLOPYRIMIDINONE COMPOUND, AND PHARMACEUTICAL COMPOSITION CONTAINING THE SAME, PREPARATION METHOD AND USE THEREOF

CROSS-REFERENCE TO RELATED APPLICATIONS

This application represents the national stage entry of PCT International Application No. PCT/CN2012/001082 filed Aug. 14, 2012, which claims the benefit of Chinese Patent Application No. 201110236585.3 filed Aug. 17, 2011, both of which are incorporated herein by reference in their entirety for all purposes.

TECHNICAL FIELD

The present invention relates to a salt and polymorph of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-d]pyrimidin-7-one (compound Z), the pharmaceutical compositions containing the same, the method for preparation of various salts and polymorphs and the use thereof in the preparation of a pharmaceutical composition.

BACKGROUND OF THE INVENTION

It discloses the use of a class of pyrazolo[4,3-d]pyrimidine-7-one derivatives as cGMP-specific phosphodiesterase inhibitors to treat erectile dysfunction in the international application WO9428902 (CN1124926A). Then in WO0227848 (CN1325398T), it discloses another class of pyrazolo[4,3-d]pyrimidine-7-one derivatives having a potent inhibitory activity for type V of phosphodiesterase (PDE5), which can be used for the treatment of diseases relevant to PDE enzymes.

A series of compounds having inhibitory activity against PDE5 are disclosed in the international application WO2007056955, which exhibit extremely high activity and selectivity for the PDE5 enzyme in the screening test in vitro of enzyme inhibitors and in which the compound 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-d]pyrimidin-7-one (compound Z, in the Example 80 in WO2007056955) represented by the following formula is included:

Compound Z

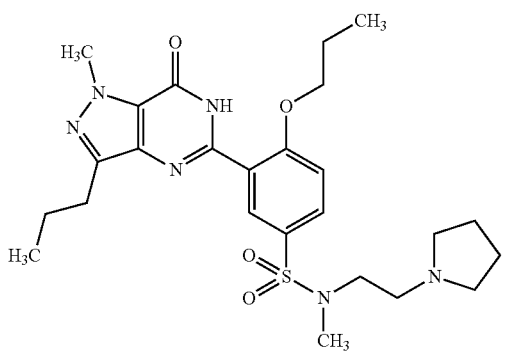

However, the compound will significantly degrade at high temperature and in bright light, and has poor chemical stability. Therefore it is particularly important to develop a stable form of the compound Z. Moreover, the compound has disadvantage with poor water-solubility and is difficult to be dissolved, which will cause some negative impact on the pharmaceutical preparation process. On the other hand, the compound itself has a pungent odor, which also has a negative impact on the application as pharmaceutical preparations for human. Therefore, the object of the invention is to develop a form of compound Z suitable for preparing the medicine, which should have good stability, high water solubility, low hygroscopicity, no pungent odor and so on.

The physical properties of pharmaceutical compounds and salts thereof, as well as their crystals and amorphous thereof have a greater impact on the bioavailability of the drugs, the purity of the drug substance, prescription of preparations etc. So in the pharmaceutical development, it is necessary to study what kinds of salts, crystalline forms, amorphous of the compounds are best to be as a drug. That is, since the above-described physical properties depend on the characteristics of the various compounds, it is usually difficult to predict pharmaceutically acceptable salts, crystals, and amorphousness of the original substances having good properties; therefore there is a sustained need to study a variety of compounds.

Thus, one object of the invention is to provide various salts, crystals and amorphousness of compound Z. In addition, another object of the invention is to provide crystals and amorphousness of compounds (I).

Based on the deeply study on synthesis and separation of various salts and crystals of the compound Z, and researching work on the physical and chemical properties thereof, the present inventors found the forms of salts, crystals and solvate of compound Z having excellent physical properties, which can be used as raw material for medicine directly or intermediates for the manufacture of pharmaceutical raw materials, thereby completing the present invention.

SUMMARY OF THE INVENTION

The present invention relates to a new salt of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-d]pyrimidin-7-one (compound Z), and pharmaceutically acceptable polymorph, solvate, hydrate, dehydrate, co-crystal, anhydrid, or amorphous form thereof, the pharmaceutical compositions and a pharmaceutical unit dosage form containing the same. The invention further relates to co-crystals or complexes of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-d]pyrimidin-7-one and pharmaceutical compositions containing the same. The present invention also relates to a process for the preparation thereof.

According to one aspect of the present invention, an object of the present invention is to provide a salt of compound 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-d]pyrimidin-7-one and the cocrystallization form thereof, having high stability, low moisture absorption, high purity, and being more readily formulated in pharmaceutical processing.

According to one aspect of the present invention, A further object of the present invention is to provide a compound represented by formula (I) (i.e. the acid addition salts of compound 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one and acid X)

and pharmaceutically acceptable polymorph, solvate, hydrate, dehydrate, co-crystal, anhydrid, or amorphous form thereof:

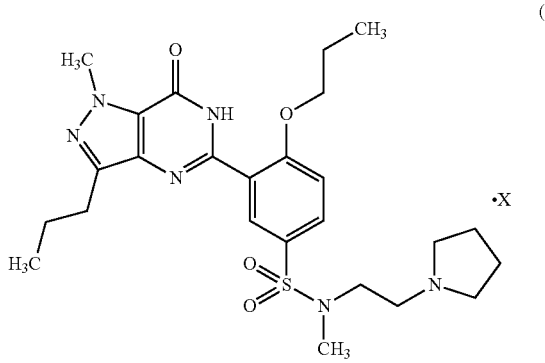

Wherein, X includes, but not limited to, organic or inorganic acid. For example, the organic acid includes, but not limited to, maleic acid, succinic acid, citric acid, tartaric acid, fumaric acid, formic acid, acetic acid, propionic acid, malonic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphanic acid, camphorsulfonic acid, salicylic acid, acetyl salicylic acid, aspartic acid, glutamic acid, lactic acid, gluconic acid, vitamin C acid, gallic acid, mandelic acid, malic acid, sorbic acid, trifluoroacetic acid, taurine, high taurine, 2-hydroxy ethyl sulfonic acid, cinnamic acid. The inorganic acid includes, but not limited to, hydrochloric acid, hydrobromic acid, hydroiodic acid, sulfuric acid, nitric acid, phosphoric acid, perchloric acid; and the similar protic acid.

Wherein, X is preferably selected from the group consisting of an organic acid, hydrochloric acid, nitric acid and sulfuric acid.

X is more preferably selected from the group consisting of maleic acid, succinic acid, citric acid, methanesulfonic acid, hydrochloric acid, nitric acid and sulfuric acid.

X is more preferable maleic acid or succinic acid.

The most preferable compound represented by formula (I) is the crystalline form A of maleate of compound Z.

The term of "salt" described herein includes the pharmaceutically acceptable salts and pharmaceutically unacceptable salts. The pharmaceutically unacceptable salts are not preferable to be administrated to the patient, however they may be used to provide the pharmaceutical intermediates and a pharmaceutical bulk drug form.

The term of "pharmaceutically acceptable salts" or "pharmaceutically acceptable acid addition salt" refers to salts prepared by using different pharmaceutically acceptable acid. The salts include, but not limited to, organic salts and inorganic salts, preferably, which are the salts of maleic acid, succinic acid, citric acid, methanesulfonic acid, hydrochloric acid, nitric acid or sulfuric acid, and is most preferably the salts of maleic acid or succinic acid.

Another embodiment of the present invention relates to pharmaceutical compositions and dosage forms containing therapeutically or prophylactically effective amount of the pharmaceutically acceptable salts of compound 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D] pyrimidin-7-one, or a polymorph, solvate, hydrate, dehydrate, co-crystal, anhydrid, or amorphous form.

Optionally, the acid addition salt of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D] pyrimidin-7-one can absorb moisture to form a hydrate with planar water by placing in the air or by recrystallization. Such acid addition salts containing such moisture are still included in the present invention.

The solvent in "solvate" in the present invention may be any solvent used in the manufacture of the salts and crystallization and is not particularly limited. Specifically, for example the solvate may be hydrate, alcoholate, acetone solvate or toluene solvate, and preferably hydrate or alcoholate.

A further embodiment of the invention relates to the preparation method of the pharmaceutical composition and dosage form comprising a therapeutically or prophylactically effective amount of the pharmaceutically acceptable salt of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one, or a polymorph, solvate, hydrate, dehydrate, co-crystal, anhydrid, or amorphous form thereof. The particular preparation method is as follows:

1. Preparation Method for the Salt of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one (Compound Represented by Formula I)

Referring to Preparation Example 80 of WO2007056955, the compound 1-methyl-5-{2-propoxy-5-[[1-methyl-1-(2-pyrrolidin-1-yl)ethyl]aminosulfonyl]pheny 1}-3-propyl-1,6-dihydro-7H-pyrazolo[4,3-D]pyrimidin-7-one (compound Z) is prepared. The compound represented by formula (I) can be prepared as the salt by reacting the corresponding acid with compound Z, the method of the present invention is as follows:

Method I:
1) Dissolving compound Z in a first solvent to form a solution a;
2) Dissolving a corresponding acid X in a second solvent to form a solution b;
3) Adding the solution a to the solution b, or adding the solution b to the solution a, so as to obtain a mixed solution, and then separating the salt of the compound Z from the mixed solution (i.e., a compound represented by formula I);

Method II:
1) Dissolving compound Z in a first solvent to form a solution a;
2) Adding a corresponding acid X directly to the solution a, and then separating the salt of the compound Z from the solution (i.e., a compound represented by formula I);

Method III:
1) Dissolving a corresponding acid X in a second solvent to form a solution b;
2) Adding compound Z directly into the solution b, and then separating the salt of the compound Z from the solution (i.e., a compound represented by formula I);

In the above-described method, the first and second solvents may be each independently selected from water, non-aqueous solvent or the mixed solvent thereof, more particularly, include water, alcohols, ethers, esters, hydrocarbons, ketones. The first and second solvents may each independently select from one or more of water; esters (such as ethyl acetate, methyl acetate, propyl acetate, butyl acetate, methyl formate, ethyl formate, propyl formate, butyl formate); alcohols (such as methanol, ethanol, propanol, isopropanol, butanol, ethylene glycol, propylene glycol); ethers (such as diethyl ether, dipropyl ether, diisopropyl ether, petroleum ether, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, dioxane, dimethoxyethane, diethylene glycol dimethyl ether); ketones (such as acetone, butanone, N-methylpyrrolidone, diethyl ketone); hydrocarbons (such as n-pentane, n-hexane, heptane); aromatic hydrocarbons (such as toluene, benzene, xylene, chlorobenzene, dichlorobenzene); alkylogen (such as methylene chloride, chloroform or 1,2-dichloroethane, carbon tetrachloride); acids (acetic acid, propionic acid); and nitriles (such as acetonitrile, propionitrile).

The definition of the corresponding acid is same as the definition of X in formula (I).

The reaction temperature may be varied according to the reagents or solvents, etc., and is generally from $-20°$ C. to $200°$ C., preferably from $0°$ C. to $100°$ C.

The reaction time is not limited and usually from 10 minutes to 10 hours.

2. The Preparation Method for Various Crystalline Forms of Compound Z (Compound Represented by Formula I)

Another aspect of the present invention provides a polymorph and solvate of the salt of Compound Z (Compound represented by formula I) and a preparation method thereof. In the mentioned method, the seed crystal may be added as necessary in the process. The "seed crystal" herein refers to "seed" of the compound represented by formula (I) or a homemade crystal material of the compound represented by formula (I), which is used to induce crystallization.

Method I
1) Dissolving compound Z in a third solvent to form a solution C;
2) Dissolving a corresponding acid X in a fourth solvent to form a solution D;
3) Adding the solution C into the solution D, or adding the solution D into the solution C, or adding the corresponding acid X directly into the solution C, so as to obtain a mixed solution E;
4) Optionally, adding a fifth solvent into the mixed solution E;
5) Precipitating the target crystal by standing, stirring or adding corresponding seed crystal into the solution prepared in step 4);

Method II
1) Dissolving the salt of compound Z (compound represented by formula (I)) in the third solvent to form solution F;
2) Optionally, adding the fifth solvent into the solution F;
3) Precipitating the target crystal by standing, stirring or adding corresponding seed crystal into the solution prepared in step 2);

Method III
1) Suspending the salt of compound Z (compound represented by formula (I)) in the third solvent to form suspension G;
2) Optionally, adding the fifth solvent into the solution G;
3) Precipitating the target crystal by heating, stirring and cooling the obtained solution, or adding seed crystal into the solution prepared in step 2);

Wherein, the third solvent, the fourth solvent and the fifth solvent may be same or different. And the definitions of the third, fourth and fifth solvents are same as those of the above first and second solvents. The range of reaction temperature is same as that for preparing the salt of the compound Z (compound represented by formula I).

In particular, the preferred method for preparing the crystalline form A of compound Z maleate is as follows:

Compound Z is suspended in alcohol and heated to $65°$ C., then one equivalent of maleic acid is added therein, and the mixture is heated under temperature of $65°$ C. for 0.5 to 3 hours. Optionally, active carbon is added to perform the decolorizing. And the resulting filtrate solution is allowed to stand or be stirred at room temperature so as to precipitate the solid, after that, the solid precipitate is isolated, i.e. crystalline form A of the compound Z maleate, which may be isolated by conventional means from the reaction mixture.

3. Characterization of Crystalline Type of the Salt of Compound Z (Compound Represented by Formula I) in the Polymorph In general, the diffraction angle (2θ) in X-ray powder diffraction may have a deviation of ±0.2°. Therefore, the following values of the diffraction angle should be understood to include a range of containing a deviation of ±0.2°. Accordingly, the present invention includes not only the crystals which are identically consistent with the X-ray powder diffraction peaks (diffraction angle), and but also the crystals consistent with the peak (diffraction angle) with a deviation of ±0.2°.

(1) Characterization of Crystalline Form A of Compound Z Maleate

The present invention provides a crystalline form A of compound Z maleate.

The data of DSC spectrum (FIG. 1) of the crystalline form A of compound Z maleate are as follows:

The initial value (Onset)=166.164±1° C., Peak value (Peak)=168.166±1° C.

The melting point of the crystalline form A of compound Z maleate is between 162±2° C. and 163±2° C.

The data of X-ray powder diffraction pattern (see FIG. 2) of crystalline form A of maleate of compound Z are as follows (Table 1): the 2θ diffraction angle is used to express X-ray powder diffraction, wherein the crystalline form has diffraction peaks at 6.30°±0.2°, 20.18°±0.2°, 22.30°±0.2° and 24.02°±0.2°.

TABLE 1

X-ray powder diffraction data of crystalline form A of maleate of compound Z

| Diffraction angle (2θ, degree) | Intensity (I/I$_0$, %) |
|---|---|
| 4.640 | 28 |
| 6.300 | 100 |
| 7.360 | 50 |
| 8.280 | 29 |
| 10.620 | 15 |
| 11.900 | 28 |
| 14.020 | 24 |
| 16.660 | 19 |
| 17.640 | 35 |

TABLE 1-continued

X-ray powder diffraction data of crystalline form A of maleate of compound Z

| Diffraction angle (2θ, degree) | Intensity (I/I₀, %) |
|---|---|
| 18.760 | 21 |
| 20.180 | 82 |
| 22.300 | 60 |
| 24.020 | 49 |
| 24.280 | 36 |
| 25.160 | 29 |
| 27.800 | 21 |
| 28.340 | 17 |

(2) Characterization of the Amorphous Form of Compound Z Maleate

Figure 3:
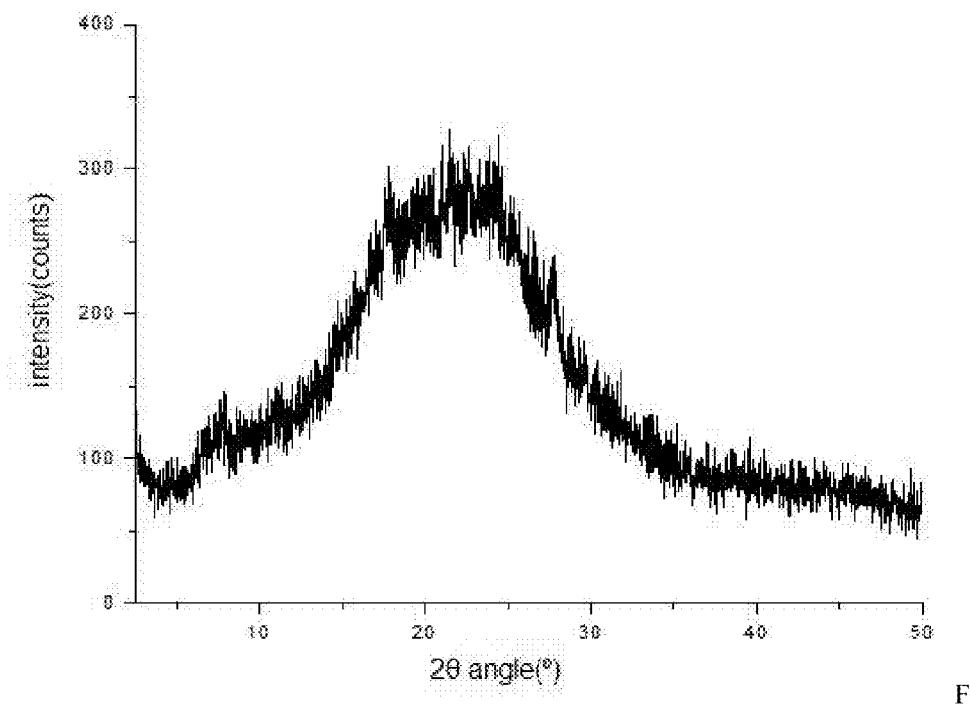

The present invention provides an amorphous form of compound Z maleate, the X-ray powder diffraction pattern of which is shown in FIG. 3.

(3) Characterization of the Crystalline Form I of Compound Z Succinate

The present invention provides a crystalline form I of compound Z succinate.

The data of DSC spectrum (FIG. 4) of compound Z succinate are as follows:

The initial value (Onset)=151.214±1° C., Peak value (Peak)=154.166±1° C.

The melting point of the crystalline form I of compound Z succinate is between 148±2° C. and 149±2° C.

The data of X-ray powder diffraction pattern (FIG. 5) of the crystalline form I of compound Z succinate are as follows (Table 2): the 2θ diffraction angle is used to express X-ray powder diffraction, wherein the crystalline form has diffraction peaks at 6.42°±0.2°, 8.00°±0.2°, 18.34°±0.2° and 24.56°±0.2°.

TABLE 2

X-ray powder diffraction data of crystalline form I of the compound Z succinate

| Diffraction angle (2θ, degree) | Intensity (I/I₀, %) |
|---|---|
| 5.520 | 23 |
| 6.420 | 100 |
| 8.000 | 89 |
| 11.060 | 70 |
| 11.600 | 52 |
| 11.940 | 43 |
| 12.220 | 29 |
| 12.880 | 33 |
| 14.280 | 21 |
| 16.060 | 25 |
| 17.140 | 21 |
| 18.340 | 86 |
| 18.860 | 35 |
| 19.080 | 38 |
| 19.380 | 65 |
| 20.280 | 59 |
| 20.740 | 52 |
| 22.220 | 39 |
| 23.360 | 39 |
| 24.080 | 36 |
| 24.560 | 87 |
| 24.880 | 59 |
| 25.180 | 78 |
| 25.840 | 26 |
| 26.180 | 20 |

(4) Characterization of the Crystalline Form I of Compound Z Methanesulfonate

The present invention provides the crystalline form I of compound Z methanesulfonate.

The data of X-ray powder diffraction pattern (FIG. 6) of the crystalline form I of compound Z methanesulfonate are as follows (Table 3): the 2θ diffraction angle is used to express X-ray powder diffraction, wherein the crystalline form has diffraction peaks at 6.62°±0.2°, 17.94°±0.2°, 22.24°±0.2° and 26.45°±0.2°.

TABLE 3

X-ray powder diffraction data of crystalline form I of the compound Z methanesulfonate

| Diffraction angle (2θ, degree) | Intensity (I/I₀, %) |
|---|---|
| 6.615 | 100.0 |
| 15.819 | 17.6 |
| 16.143 | 16.3 |
| 17.942 | 35.5 |
| 18.472 | 19.2 |
| 22.238 | 28.9 |
| 26.452 | 19.7 |

(5) Characterization of the Crystalline Form I of Compound Z Hydrochloride

The present invention provides a crystalline form I of compound Z hydrochloride.

The data of DSC spectrum (FIG. 7) of the crystalline form I of compound Z hydrochloride are as follows:

Peak 1: Initial value (Onset)=137.331±1° C., Peak value (Peak)=143.000±1° C.

Peak 2: Initial value (Onset)=197.891±1° C., Peak value (Peak)=201.333±1° C.

The data of X-ray powder diffraction pattern (FIG. 8) of the crystalline form I of compound Z hydrochloride are as follows (Table 4): the 2θ diffraction angle is used to express X-ray powder diffraction, wherein the crystalline form has diffraction peaks at 7.21°±0.2°, 8.05°±0.2°, 12.44°±0.2° and 16.32°±0.2°.

TABLE 4

X-ray powder diffraction data of crystalline form I of the compound Z hydrochloride

| Diffraction angle (2θ, degree) | Intensity (I/I₀, %) |
|---|---|
| 7.212 | 100.0 |
| 8.047 | 52.6 |
| 12.444 | 28.3 |
| 13.050 | 21.9 |
| 16.323 | 22.3 |
| 17.943 | 16.9 |
| 23.993 | 21.5 |
| 25.405 | 19.1 |

(6) Characterization of the Crystalline Form II of Compound Z Hydrochloride

The present invention provides a crystalline form II of compound Z hydrochloride.

The data of DSC spectrum (FIG. 9) of the crystalline form II of compound Z hydrochloride are as follows:

The initial value (Onset)=194.168±2° C., Peak value (Peak)=196.000±2° C.

The data of X-ray powder diffraction pattern (FIG. 10) of the crystalline form II of compound Z hydrochloride are as follows (Table 5): the 2θ diffraction angle is used to express X-ray powder diffraction, wherein the crystalline form has diffraction peaks at 6.21°±0.2°, 19.28°±0.2°, 20.79°±0.2° and 24.45°±0.2°.

TABLE 5

X-ray powder diffraction data of crystalline form II of the compound Z hydrochloride

| Diffraction angle (2θ, degree) | Intensity (I/I₀, %) |
| --- | --- |
| 6.212 | 100.0 |
| 15.585 | 8.3 |
| 18.733 | 10.5 |
| 19.275 | 58.0 |
| 20.080 | 7.7 |
| 20.791 | 69.4 |
| 22.493 | 11.5 |
| 24.445 | 15.5 |
| 24.853 | 9.6 |

(7) Characterization of the Crystalline Form III of Compound Z Hydrochloride

The present invention provides a crystalline form III of compound Z hydrochloride.

The data of DSC spectrum (FIG. 11) of the crystalline form III of compound Z hydrochloride are as follows:

The initial value (Onset)=180.978±1° C., Peak value (Peak)=182.666±1° C.

The data of X-ray powder diffraction pattern (FIG. 12) of the crystalline form III of compound Z hydrochloride are as follows (Table 6): the 2θ diffraction angle is use to express X-ray powder diffraction, wherein the crystalline form has diffraction peaks at 7.22°±0.2°, 16.64°±0.2°, 24.86°±0.2° and 25.48°±0.2°.

TABLE 6

X-ray powder diffraction data of crystalline form III of the compound Z hydrochloride

| Diffraction angle (2θ, degree) | Intensity (I/I₀, %) |
| --- | --- |
| 5.960 | 20.1 |
| 6.801 | 21.0 |
| 7.221 | 100.0 |
| 9.499 | 17.8 |
| 16.639 | 53.8 |
| 17.920 | 19.0 |
| 24.859 | 53.8 |
| 25.480 | 34.8 |
| 26.260 | 24.2 |
| 27.560 | 21.6 |

(8) Characterization of the Crystalline Form IV of Compound Z Hydrochloride

The present invention provides a crystalline form IV of compound Z hydrochloride.

The data of DSC spectrum (FIG. 13) of the crystalline form IV of compound Z hydrochloride are as follows:

The initial temperature (Onset)=180.050±1° C., the peak temperature (Peak)=184.333±1° C.

The initial temperature (Onset)=196.715±1° C., the peak temperature (Peak)=199.333±1° C.

The data of X-ray powder diffraction pattern (FIG. 14) of the crystalline form IV of compound Z hydrochloride are as follows (Table 7): the 2θ diffraction angle is used to express X-ray powder diffraction, wherein the crystalline form has diffraction peaks at 7.41°±0.2°, 7.64°±0.2°, 17.55°±0.2° and 25.83°±0.2°.

TABLE 7

X-ray powder diffraction data of crystalline form IV of the compound Z hydrochloride

| Diffraction angle (2θ, degree) | Intensity (I/I₀, %) |
| --- | --- |
| 7.411 | 55.3 |
| 7.635 | 100.0 |
| 16.653 | 24.8 |
| 17.547 | 76.1 |
| 18.256 | 22.8 |
| 18.840 | 21.3 |
| 25.461 | 20.4 |
| 25.829 | 24.5 |
| 27.276 | 19.5 |

According to another aspect of the present invention, one object of the present invention is to provide a pharmaceutical composition comprising one or more compounds represented by formula (I) and pharmaceutically acceptable accessories, preferably a pharmaceutical composition comprising maleate, succinate, methanesulfonate, citrate, hydrochloride, sulfate of compound Z, more preferably a pharmaceutical composition comprising crystalline form A of compound Z maleate having a X-ray powder diffraction pattern shown in table 1.

The accessories may be an excipient, a binder, a lubricant, a disintegrating agent, a coloring agent, a corrective, an emulsifier, a surfactant, a solubilizer, a suspending agent, an isotonic agent, a buffering agent, preservatives, an antioxidant, a stabilizer, an absorption accelerators and the like commonly used in the pharmaceutical art, and a suitable combination of the foregoing accessories may be used if necessary.

Preferably, the salts of the compound Z of the present invention may be formulated with at least one pharmaceutical excipient in the oral pharmaceutical composition, each dosage may contain 10 mg to 200 mg of the active ingredient.

When preparing a solid composition in tablet type, the main active ingredient may be mixed with a pharmaceutical carrier such as starch, lactose, magnesium stearate, etc., or the tablet may be coated with a sugar-coating or other suitable material, or can be treated so as to allow the tablet to have a prolonged or slow releasing function, so that the tablet can release a predetermined amount of the active ingredient in a continuous manner.

Or, a capsule dosage form can be obtained by mixing the active ingredient with a diluent and filling the resulting mixture into a capsule.

When using the acid addition salts of the compound Z (compound represented by formula I) of the present invention as therapeutic agents or preventive medicines to treat the above-mentioned diseases, itself (or mixed with pharmacologically acceptable excipient or diluent etc.) can be orally administered in form of tablet, capsule, granule, powder or syrup etc., or can be non-orally administered in form of injection, injectable powder, sprays or suppositories.

These formulations may be prepared by conventional methods.

The usage amount of medicine will be different according to the symptom, age, etc., for example, an adult can be administered 1 to 7 times in one to seven days according to the symptom, the dose is 0.01 mg to 1000 mg, and the administration manner is not limited.

Another object of the present invention is to provide a use of the compound represented by the formula (I) in the preparation of a medicament for the prevention or treatment of diseases associated with PDE5 enzyme. The disease associated with PDE5 enzyme is erectile dysfunction, pulmonary hypertension, female sexual dysfunction, premature birth, dysmenorrhea, benign prostatic hyperplasia, bladder outlet obstruction, incontinence, unstable and variant angina, hypertension, congestive heart failure, renal failure, atherosclerosis, stroke, peripheral vascular disease, Raynaud's disease, inflammatory disease, bronchitis, chronic asthma, allergic asthma, allergic rhinitis, glaucoma or diseases characterized by enterocinesia disorders, etc.

BRIEF DESCRIPTION FOR FIGURES

Figure 2:
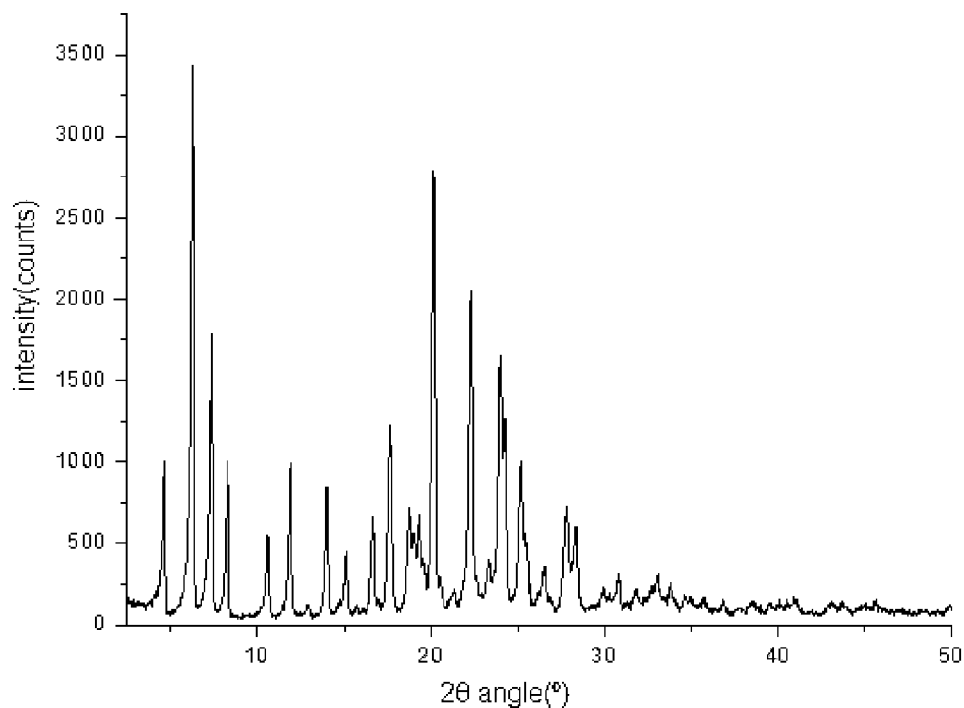
Figure 4:
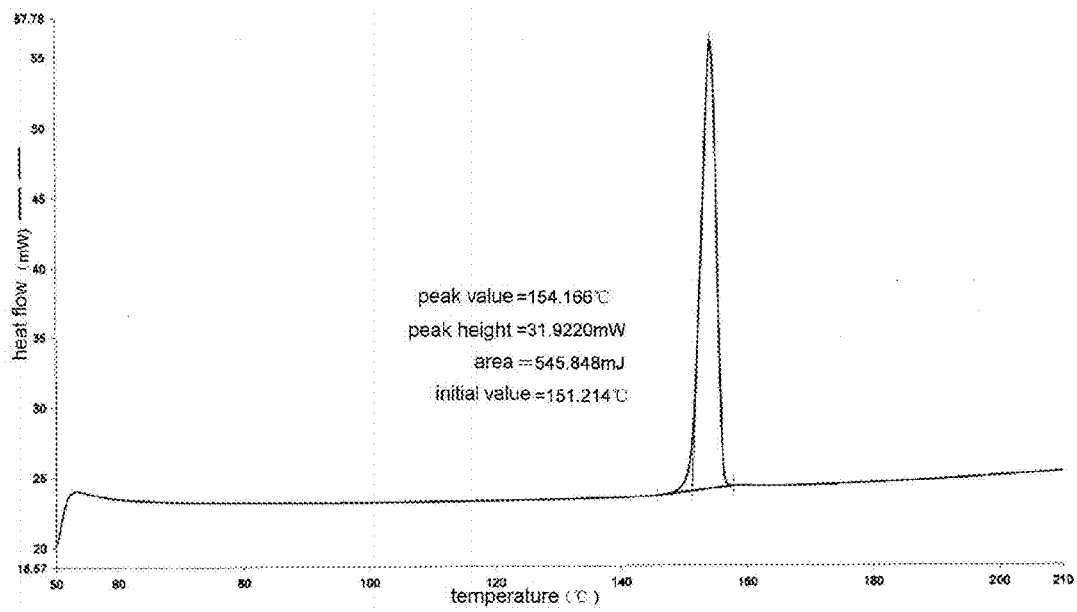
Figure 5:
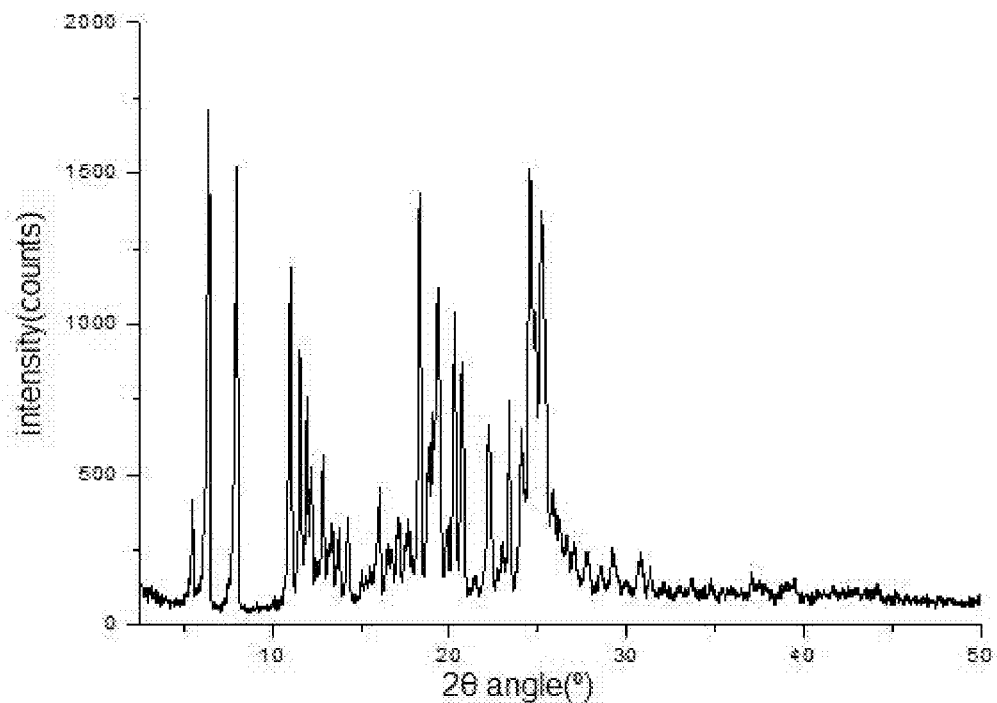
Figure 6:
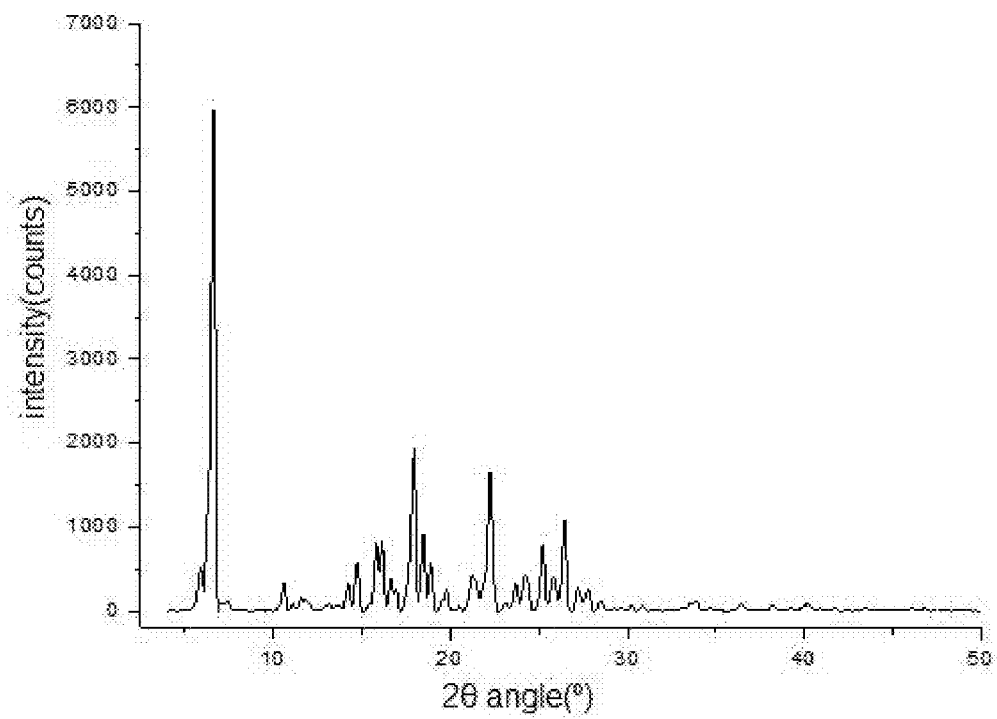
Figure 7:
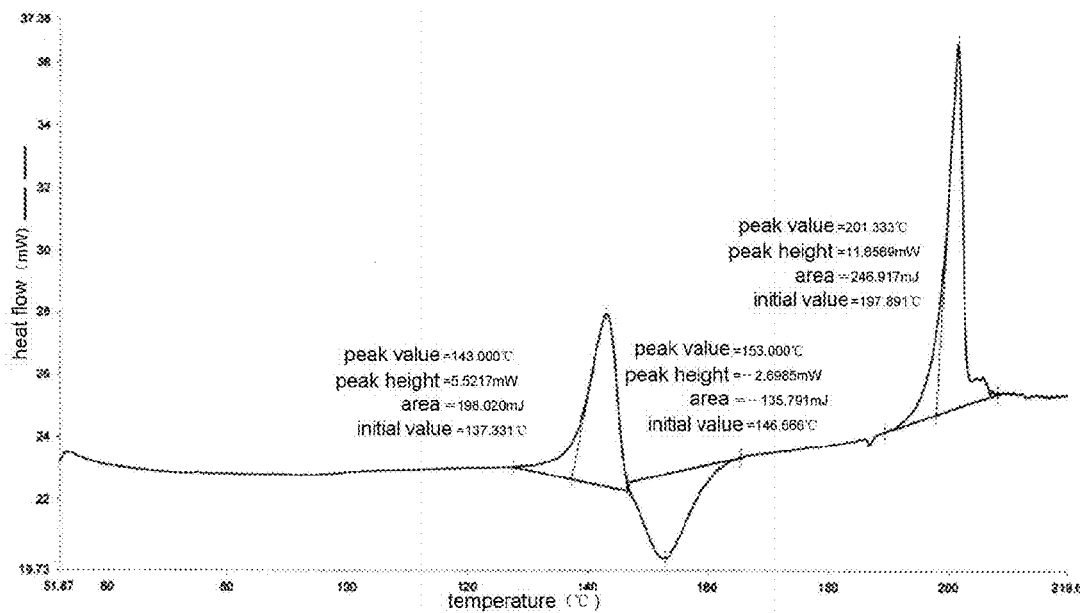
Figure 8:
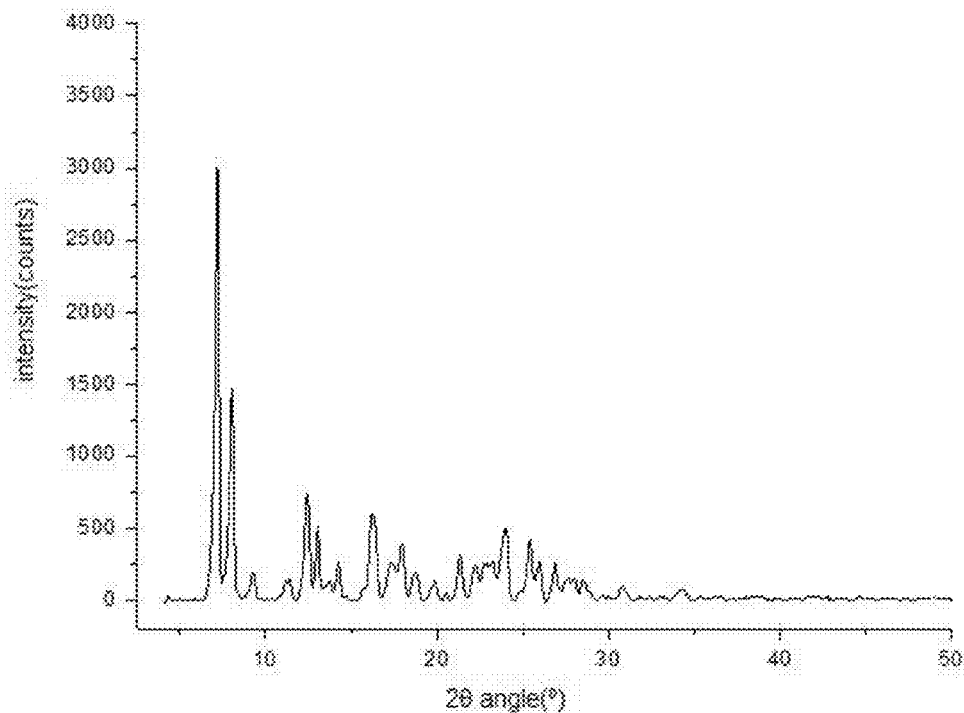
Figure 9:
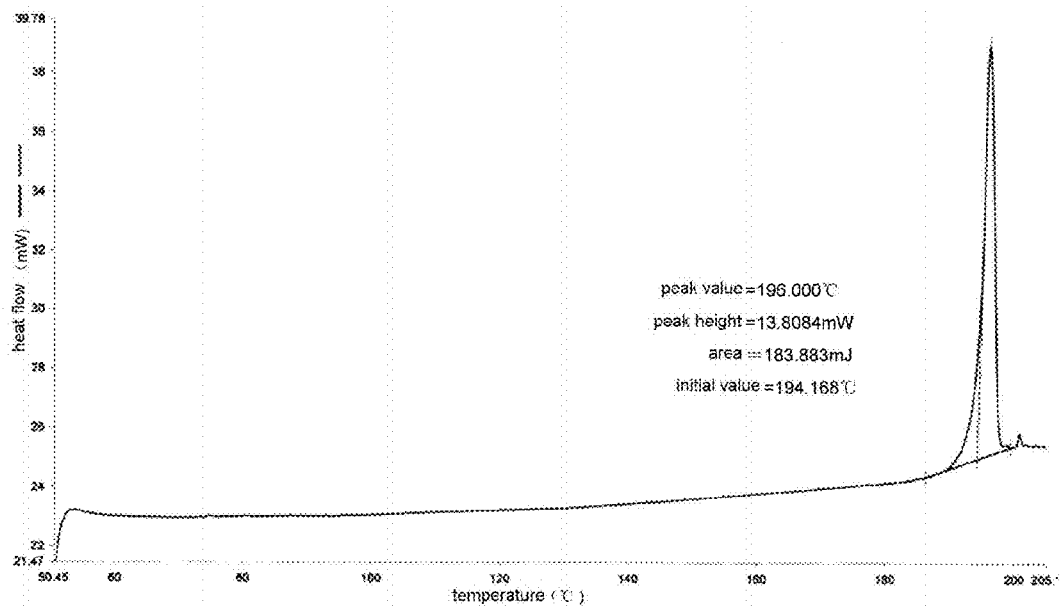
Figure 10:
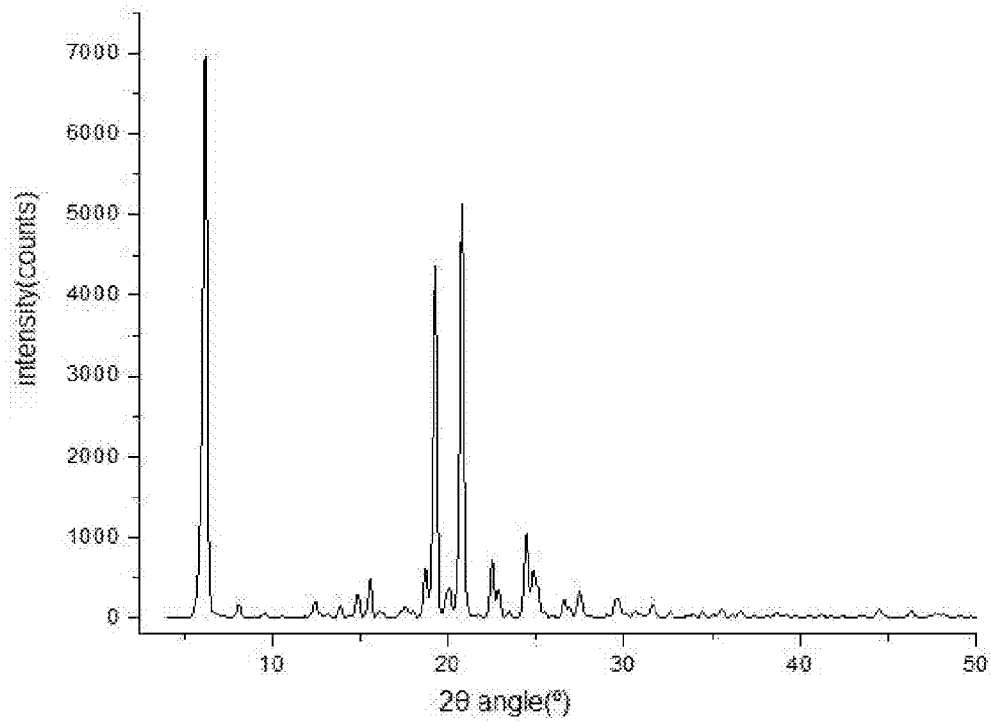
Figure 11:
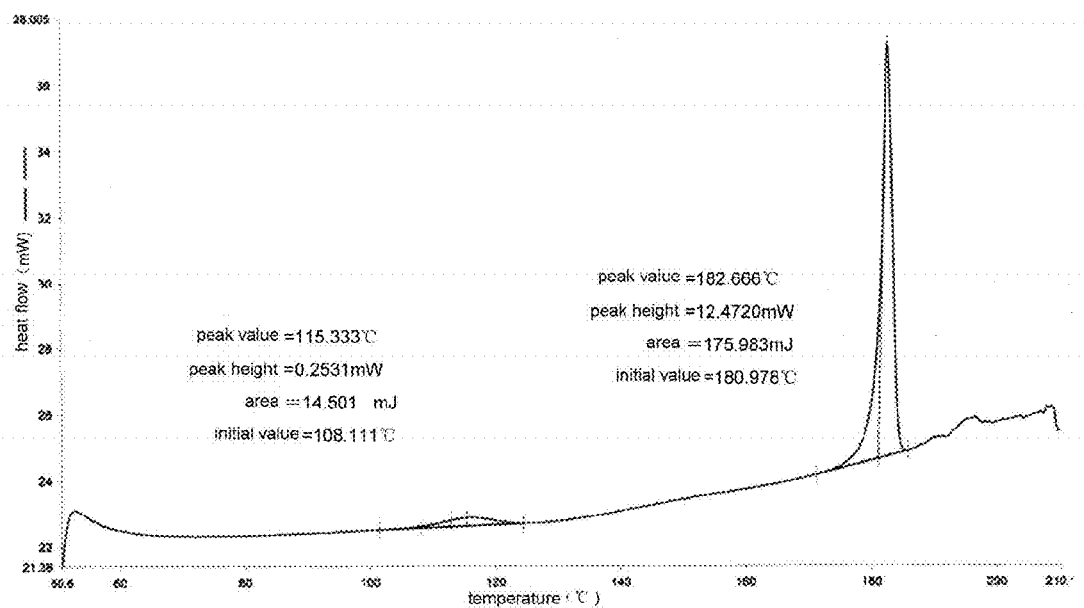
Figure 12:
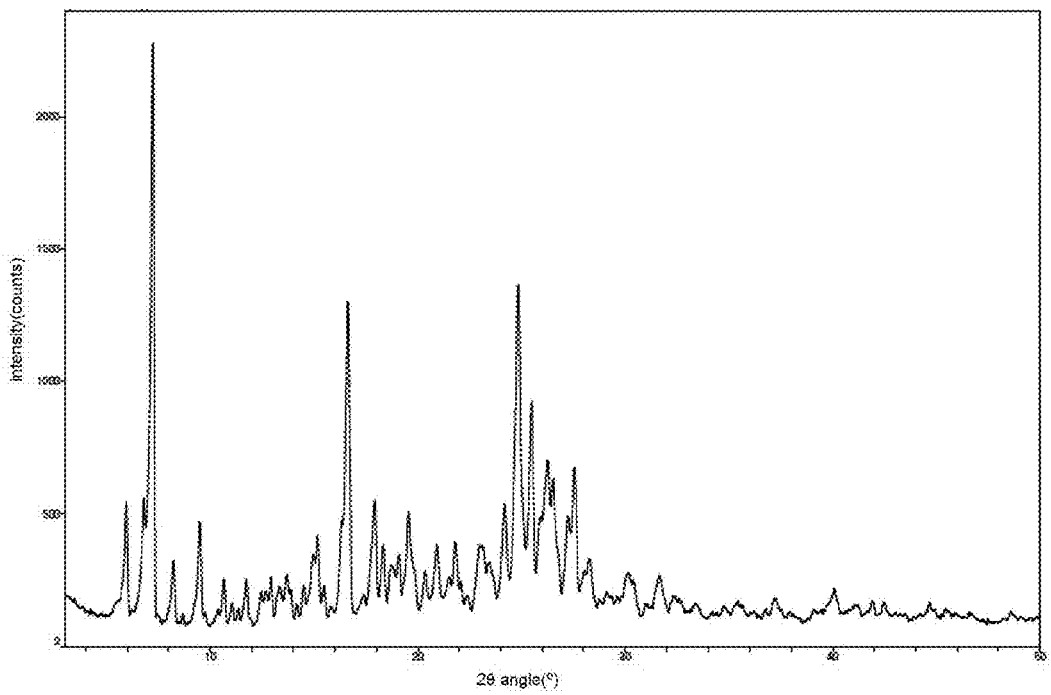
Figure 13:
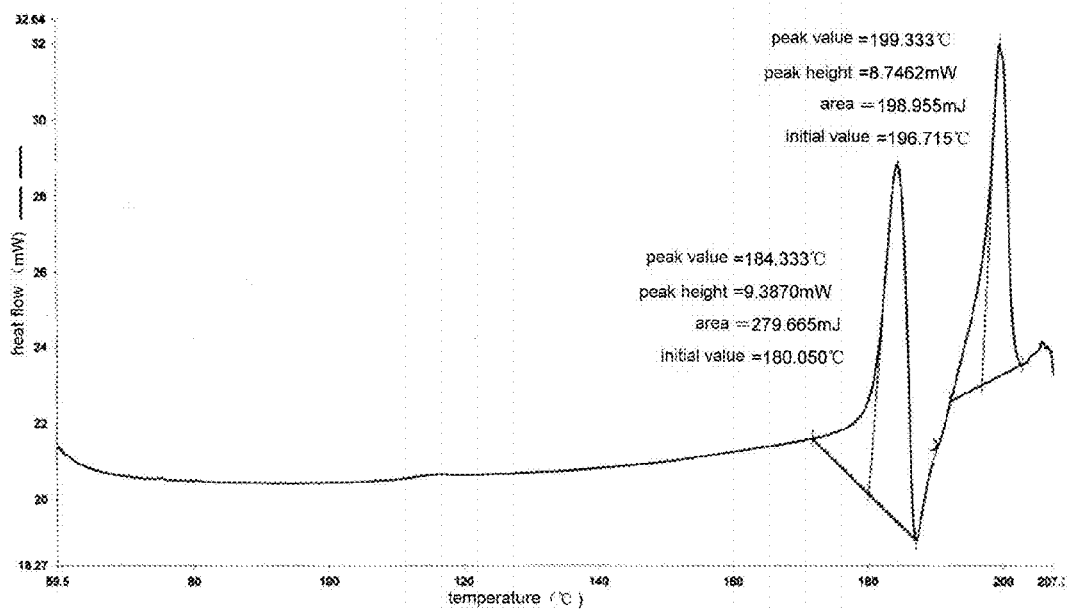
Figure 14:
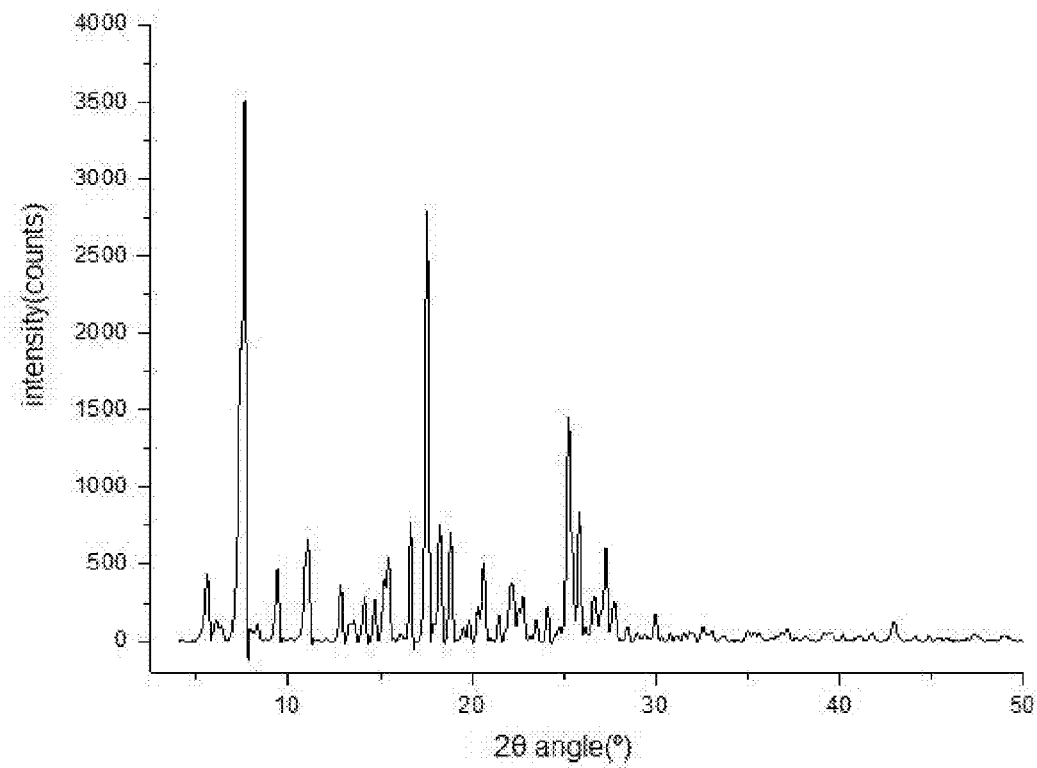
Figure 15:
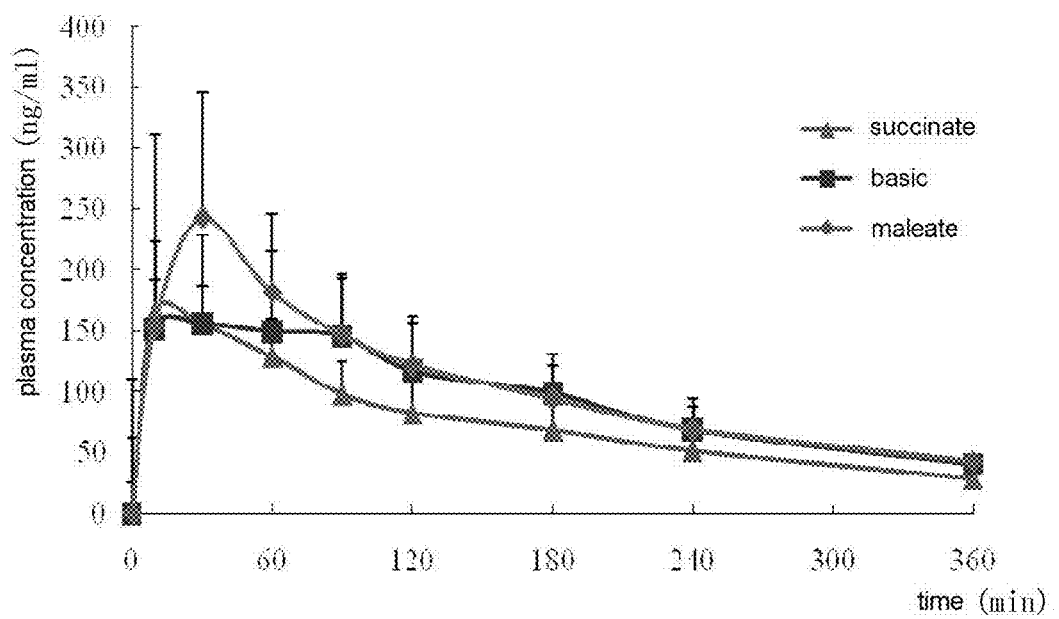
Figure 16:
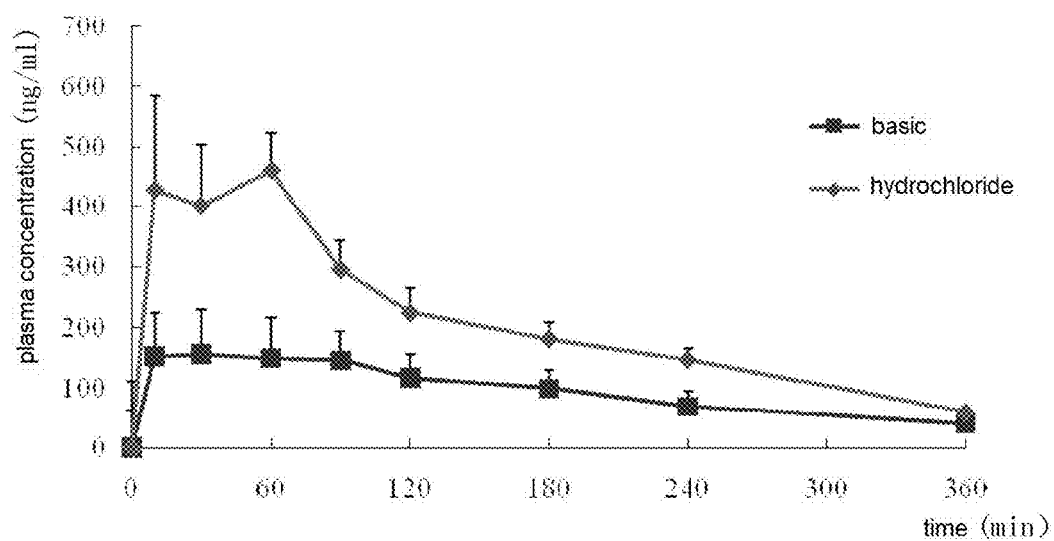
Figure 17:
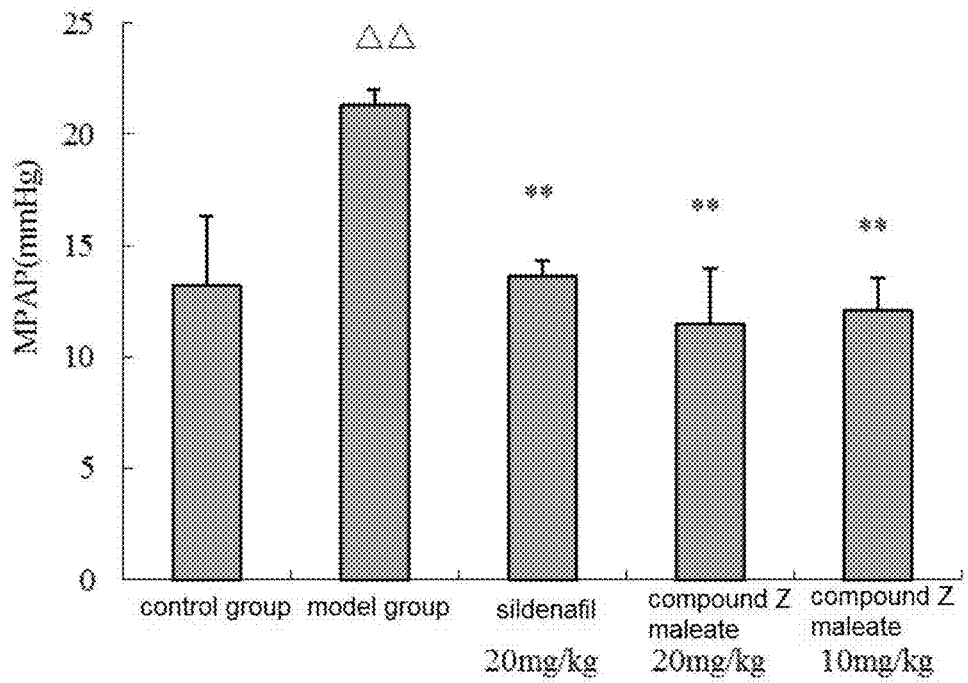
Figure 18:
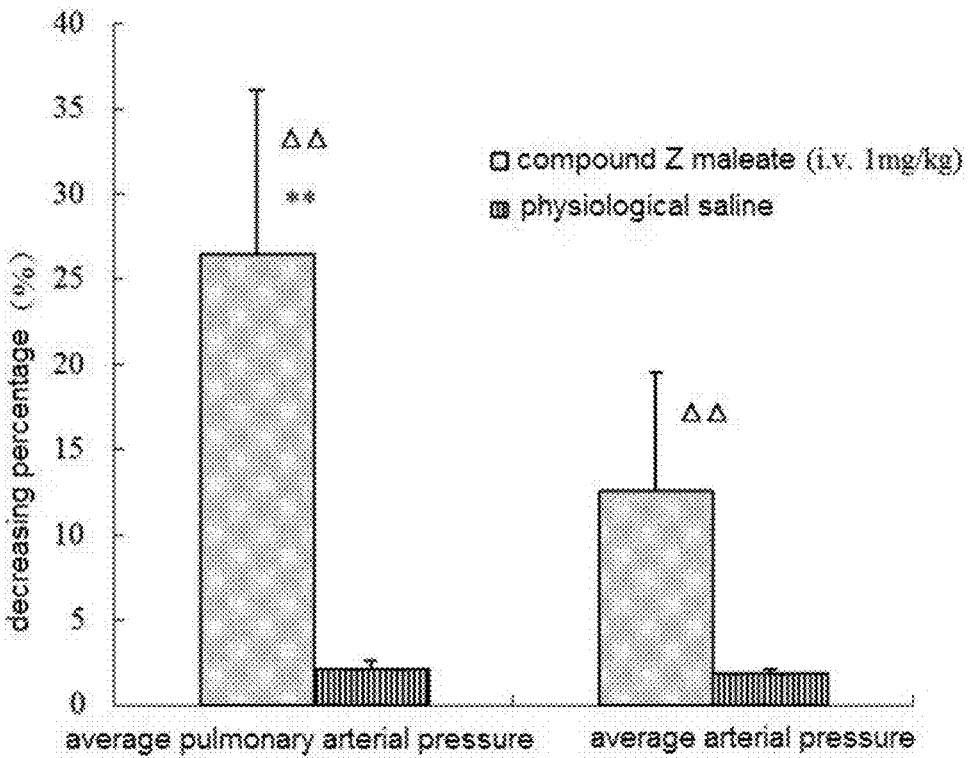
Figure 19:
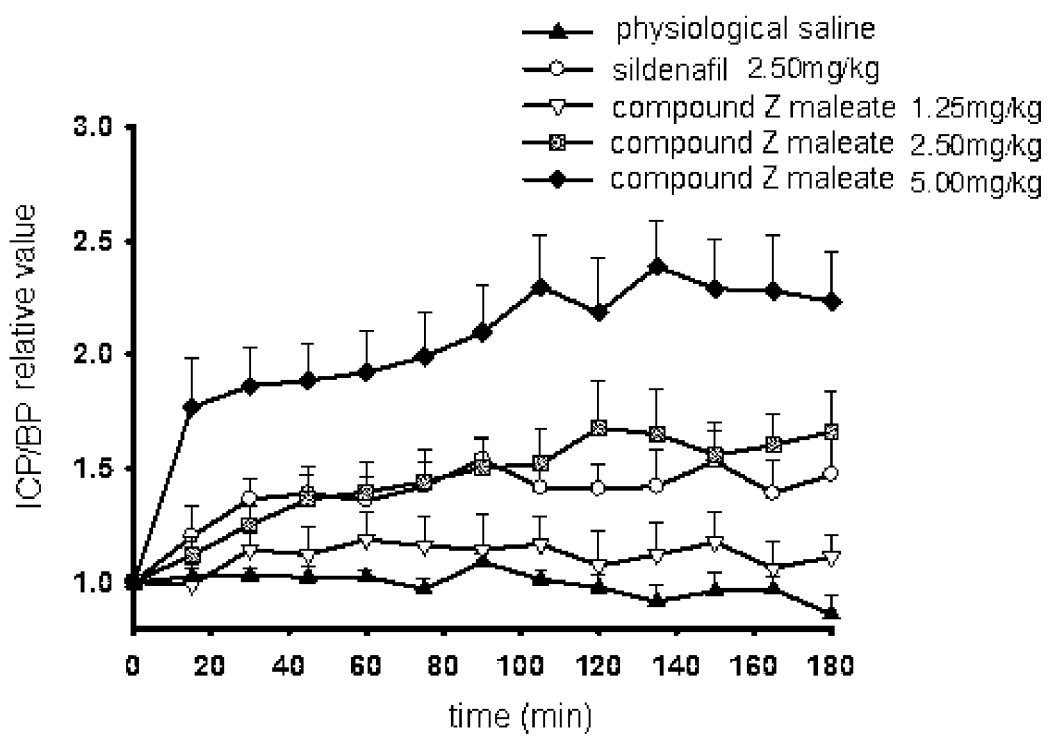
Figure 20:
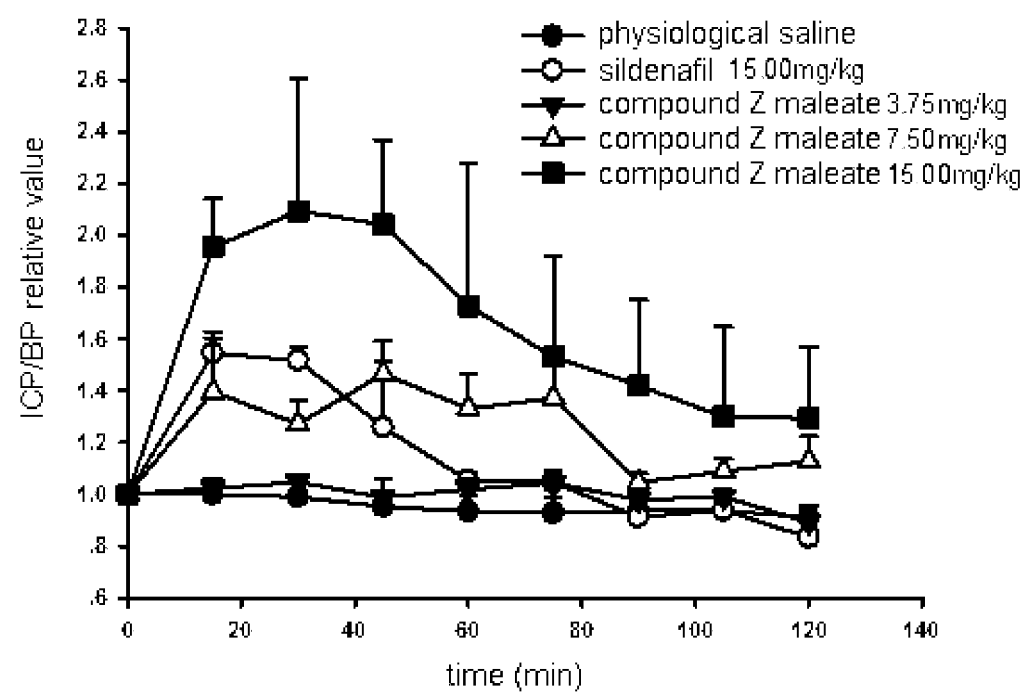

FIG. 1: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (crystalline form A);

FIG. 2: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (crystalline form A);

FIG. 3: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-p yrazolo[4,3-D]pyrimidin-7-one maleate (amorphous);

FIG. 4: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one succinate (crystalline form I);

FIG. 5: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one succinate (crystalline form I);

FIG. 6: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one methanesulfonate (crystalline form I);

FIG. 7: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form I);

FIG. 8: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form I);

FIG. 9: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form II);

FIG. 10: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form II);

FIG. 11: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-p yrazolo[4,3-D]pyrimidin-7-one hydrochloride (crystalline form III);

FIG. 12: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form III);

FIG. 13: differential thermal analysis graph of 1-methyl-5-{2-propoxy-5-[[1-methyl-1-(2-pyrrolidin-1-yl)ethyl]aminosulfonyl]phenyl}-3-propyl-1,6-dihydro-7H-p yrazolo[4,3-D]pyrimidin-7-one hydrochloride (crystalline form IV);

FIG. 14: X-ray powder diffraction pattern of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (crystalline form IV) obtained in example 23;

FIG. 15: plasma concentration-time curve after administration of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one (basic) and different salts thereof;

FIG. 16: plasma concentration-time curve after administration of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one (basic) and hydrochloride thereof;

FIG. 17: the effect of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate on the pulmonary arterial pressure in rats by chronic oral administration;

FIG. 18: the effect of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate on the pulmonary arterial pressure in rats by single intravenous administration;

FIG. 19: the pharmaceutical effect of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D] pyrimidin-7-one maleate on rats ED;

FIG. 20: the pharmaceutical effect of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D] pyrimidin-7-one maleate on canine ED.

TECHNICAL EFFECT OF THE INVENTION

The object of the present invention is to find a form of the compound having high solubility, good stability, good pharmacokinetics, and being suitable for preparing medicines. In the following experiments, unless specified, the salt of compound Z (compound represented by formula I) is suitable for all of the cryltalline form, mixed crystal, amorphous substance, and solvate thereof.

One aspect of the present invention is to provide the salt of compound Z, which has high stability, improved water solubility, no bad smell and so on.

Another aspect of the invention is to provide a plurality of crystalline forms of the various salts of compound Z. The crystalline forms have lower moisture absorption, good chemical stability, high purity, constant composition etc. The preparation method is simple and easy to repeat and the sample is easy to be stored.

Best Modes

The present invention will be further illustrated by the following examples. The following embodiments of the present invention are intend to more specifically illustrate the preferred embodiment of the present invention and should not be understood to limit the present invention. Both of the temperature and the reagent adopted in the following examples can be alternatively replaced by the corresponding temperature and reagent described above to achieve the object of the present invention.

In the following embodiments, the melting point was measured by using WRR Melting Point Meter without temperature correction; Elemental Analysis was carried out by using Elementar Vario EL instrument; the nuclear magnetic resonance spectra were measured by using Mercury- 400 and Mercury 300 NMR spectrometer (Varian Company); Mass spectra were measured by using MAT-95 mass spectrometer (Finnigan corporation); the infrared spectrum were measured by using United States Nicolet FTIR-6700 Fourier transform type infrared spectrometer; the thermal analysis was carried out by using Pyris 1 DSC (PERKIN-ELMER) apparatus; X-diffraction was carried out on Rigaku D/max-rB X rotating-target polycrystalline diffractometer or D8 ADVANCE X-RAY DIFFRACTOMETER polycrystalline diffractometer.

Example 1

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one (the compound Z, the same below) (48.5 g, 0.094 mol) was suspended in 500 ml of anhydrous ethanol and heated to 65° C. to make the sample dissolved, then added maleic acid (11.0 g, 0.095 mol), and the solution was heated under 65° C. for 40 minutes. The active carbon (2 g) was added after cooling slightly and the temperature was maintained for 30 minutes, and then the active carbon was filtered off and the obtained filtrate was stirred at room temperature for 30 minutes to precipitate solid. Then the solid was filtered, dried for 4 hours at 60° C. to give the title compound as a white solid (42 g), yield: 70.7%, Purity: 99% (HPLC). mp: 162.5-163.3° C. $^1$HNMR (CDCl3) δ: 0.99 (t, 3H), 1.16 (t, 3H), 1.80~1.86 (m, 2H), 1.99~2.04 (m, 2H), 2.12 (brs, 4H), 2.84 (s, 3H), 2.90 (t, 2H), 3.00 (brs, 2H), 3.42 (brs, 4H), 3.85 (brs, 2H), 4.24 (s, 3H), 4.26 (t, 2H), 6.22 (s, 2H), 7.20 (d, 1H), 7.84 (dd, 1H), 8.77 (d, 1H), 10.89 (brs, 1H), 12.60 (brs, 1H). EI/MS: 516 (M+), 515 (M−1). IR (cm$^{-1}$): 3293.9, 2968.0, 2873.5, 1704.8, 1619.9, 1577.5, 1490.7, 1330.7, 1164.8, 966.2, 875.5, 578.5. Elemental analysis:

|  | C | H | N | S |
|---|---|---|---|---|
| Actual measured value | 55.05 | 6.31 | 13.35 | 5.29 |
| Theoretical value | 55.05 | 6.37 | 13.28 | 5.07 |

Example 2

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one succinate The basic compound Z (50 g, 0.097 mol) was suspended in 300 ml of anhydrous ethanol and heated to 65° C. to make the sample dissolved, then added succinic acid (11.7 g, 0.099 mol), and the solution was stirred at 65° C. for 40 minutes. Then the active carbon (2 g) was added after cooling slightly to perform discoloring and it was maintained at this temperature for 30 minutes. After that, the active carbon was filtered off and the filtrate was stirred for 30 minutes at room temperature to precipitate solid. The precipitated solid was filtered and dried for 4 hours at 60° C. to give a white crystalline solid as the title compound (27 g), Yield: 44%, Purity: 99.4% (HPLC). mp: 148.6-149.6° C. $^1$HNMR (CDCl3) δ: 1.00 (t, 3H), 1.16 (t, 3H), 1.81~1.88 (m, 2H), 1.98~2.05 (brm, 6H), 2.52 (s, 4H), 2.85 (s, 3H), 2.88~2.93 (t, 2H), 3.21~3.28 (brm, 6H), 3.34~3.36 (t, 2H), 4.23~4.27 (t, 2H), 4.27 (s, 3H), 7.20 (d, 1H), 7.86 (dd, 1H), 8.73 (d, 1H), 11.00 (brs, 1H). EI MS: 515 (M−1).

Example 3

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one methanesulfonate The basic compound Z (31 g, 0.06 mol) was suspended in 200 ml of anhydrous ethanol and added 4 ml methanesulfonic acid under ice bath. After the addition was completed, the obtained mixture was increased to 60~70° C. and stirred for 30 minutes. Then the active carbon (2 g) was added to perform discoloring. After that, the active carbon was filtered off and the filtrate was concentrated to a small volume under reduced pressure. Then 400 ml ethyl acetate was added and it was stirred for 2 hours. The product gradually precipitated, and then the product was filtered off and dried at 55° C. to obtain the title compound 27.5 g. mp: 178.9-179.3° C. $^1$HNMR (CDCl3) δ: 1.00 (t, 3H), 1.17 (t, 3H), 1.81~1.90 (m, 2H), 1.99~2.06 (m, 2H), 2.12~2.20 (m, 4H), 2.75 (s, 3H), 2.91 (t, 2H), 2.93 (s, 3H), 2.96~3.02 (m, 2H), 3.45~3.55 (m, 4H), 3.89~3.94 (m, 2H), 4.27 (s, 3H), 4.24~4.29 (t, 2H), 7.19 (d, 1H), 7.87 (dd, 1H), 8.79 (d, 1H), 11.02 (brs×2, 2H). EI/MS: 515 (M−1). Elemental analysis:

|  | C | H | N |
|---|---|---|---|
| Actual measured value | 50.83 | 6.59 | 13.55 |
| Theoretical value | 50.96 | 6.58 | 13.71 |

Example 4

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one citrate The basic compound Z (5.17 g, 0.01 mol) was suspended in 25 ml of anhydrous ethanol, 2.14 g of citric acid was added and then the mixture was heated to 6070° C. and stirred for 30 minutes. After that, the mixture was cooled to room temperature and stirred overnight, and then the precipitated white solid was filtered off and dried at 55° C. to give the title compound 4.5 g, Yield: 63.4%. mp: 140° C. $^1$HNMR (CDCl3) δ: 1.00 (t, 3H), 1.16 (t, 3H), 1.81~1.88 (m, 2H), 1.98~2.05 (m, 2H), 2.12 (brm, 4H), 2.52 (s, 4H), 2.85 (s, 3H), 2.93 (t, 2H), 3.03~3.08 (brs, 2H), 3.45~3.55 (brm, 4H), 3.83 (brs, 2H), 4.27 (s, 3H), 4.23~4.27 (t, 2H), 7.19 (d, 1H), 7.86 (dd, 1H), 8.75 (d, 1H), 10.89 (brs, 1H), 11.80 (brs, 3H). EI/MS: 515 (M−1).

Example 5

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one citrate The basic compound Z (5.17 g, 0.01 mol) was dissolved in a mixed solvent of 25 ml of anhydrous ethanol and 5 ml of water, 2.14 g of citric acid was added and then the mixture was heated to 60~70° C. and stirred for 30 minutes. After that, the mixture was cooled to room temperature and stirred overnight, and then the self-made seed crystal was added to gradually precipitate the product. The obtained product was filtered off and dried at 55° C. to give the title compound 4.3 g.

Example 6

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride The basic compound Z (51.7 g, 0.1 mol) was added into acetonitrile (200 ml), and then 8.6 ml of concentrated hydrochloric acid was added therein under ice bath. After the dropping addition was completed, the mixture was heated under reflux for one hour. Then the active carbon (5 g) was added to perform the discoloring. The obtained mixture was filtered, and the filtrate was cooled to room temperature and stirred to gradually precipitate the product. The precipitated product was filtered off and dried at 55° C. to give 35 g of the title compound as a white solid, Yield: 63.2%. $^1$HNMR (CDCl3) δ: 1.01 (t, 3H), 1.18 (t, 3H), 1.81~1.88 (m, 2H), 1.98~2.08 (q, 2H), 2.10~2.25 (brm, 4H), 2.91 (t, 2H), 2.95 (s, 3H), 3.42 (brs, 2H), 3.57~3.61 (brm, 2H), 3.84 (brs, 2H), 4.27 (s, 3H), 4.25~4.30 (t, 2H), 7.19 (d, 1H), 7.86 (dd, 1H), 8.83 (d, 1H), 10.84 (brs, 1H), 12.57 (brs, 1H). EI/MS: 515 (M−1).
Elemental analysis:

|  | C | H | N |
|---|---|---|---|
| Actual measured value | 54.14 | 6.64 | 15.25 |
| Theoretical value | 54.29 | 6.74 | 15.19 |

Example 7

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride The basic compound Z (51.7 g, 0.1 mol) was suspended in a mixed solvent of 400 ml of anhydrous ethanol and 10 ml of water, 8.6 ml of concentrated hydrochloric acid was added therein under ice bath. After the dropping addition was completed, the mixture was heated to 60° C. for 30 minutes. The active carbon (5 g) was added and it was stirred for 30 minutes. Then the filtration was performed to remove the active carbon. Some solvent was removed by concentration under reduced pressure, then 600 ml ethyl acetate was added to gradually precipitate the product. The obtained product was filtered off and dried at 55° C. to give the title compound 31 g.

Example 8

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one sulfate The basic compound Z (5 g) was dissolved in 19 ml of anhydrous ethanol and 0.5 ml of water, then 0.7 ml of concentrated sulfuric acid was added under ice bath, and the mixture was heated under reflux for 30 minutes, then naturally cooled to room temperature and concentrated to a small volume under reduced pressure. Then 30 ml of ethyl acetate was added to perform precipitation. The precipitated product was filtered off and dried at 55° C. to obtain 3.5 g of product. EI/MS: 515 (M−1).
Elemental analysis:

|  | C | H | N |
|---|---|---|---|
| Actual measured value | 48.61 | 6.32 | 13.82 |
| Theoretical value | 48.85 | 6.23 | 13.67 |

Example 9

The Preparation of ½ maleate of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one The basic compound Z (5.17 g) was suspended in 19 ml of anhydrous ethanol and 1 ml of water, then the suspension was heated to 60~70° C. to dissolve the compound. 0.59 g of maleic acid was added, the mixture was heated for further 30 minutes, naturally cooled to room temperature and concentrated to a small volume under reduced pressure. Then 40 ml of ethyl acetate was added to gradually precipitate the product. The precipitated product was filtered off and dried at 55° C. to obtain 4.6 g of product.

Example 10

The Preparation of ½ succinate of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one The basic compound Z (5 g) was added into 19 ml of anhydrous ethanol and 1 ml of water, then the mixture was heated to 60~70° C. to dissolve the compound. 0.58 g of succinic acid was added, the mixture was heated for further 30 minutes, naturally cooled to room temperature and concentrated to a small volume under reduced pressure. The product gradually precipitated and the precipitated product was filtered off and dried at 55° C. to obtain 2.1 g of the title compound. mp: 130.5~136.6° C.
Elemental analysis:

|  | C | H | N |
|---|---|---|---|
| Actual measured value | 56.07 | 6.82 | 14.21 |
| Theoretical value | 56.33 | 6.83 | 14.60 |

Example 11

The Preparation of ⅓ citrate of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one The basic compound Z (5 g) was added into 19 ml of anhydrous ethanol and 1 ml of water, then the mixture was heated to dissolve the compound. And then 0.69 g of citric acid was added, the mixture was heated at 60° C. for further 30 minutes, naturally cooled to room temperature and concentrated to a small volume under reduced pressure. Then 30 ml of ethyl acetate was added to gradually precipitate the product. The precipitated product was filtered off and dried at 55° C. to obtain 4.0 g of the title compound. mp: 148° C.

Examples 12 to 32

The Preparation of Various Crystalline Forms of Salts of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one General Method: 0.5 to 1.5 g sample salts of the compound Z were dissolved in various solvents (including single solvent and mixed solvents) and allowed to stand to precipitate. Or the sample salts were suspended in a solvent (including single solvent and mixed solvents) and the suspension was stirred, optionally added with another solvent if necessary, to precipitate. The precipitated solid was filtered off and dried to obtain the title compound.

Example 12

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (Crystalline Form A)

The compound of Example 1 was dissolved in ethanol, and allowed to stand to precipitate a white needle crystal. The obtained crystal was filtered off and dried to give the title compound. mp: 162.5-163.3° C., DSC graph thereof was shown in FIG. 1, and X-ray powder diffraction pattern was shown in FIG. 2.

Example 13

The Preparation of Maleate of Compound Z (Crystalline Form A)

The compound of Example 1 was dissolved in ethanol, and ethyl acetate was added to precipitate. The obtained precipitation was filtered off and dried to give the title compound. The data of mp, DSC graph, and X-ray powder diffraction pattern were same as those shown in Example 12.

Example 14

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (Crystalline Form A)

The compound of Example 1 was dissolved in acetone by heating, and allowed to stand to precipitate. The obtained precipitation was filtered off and dried to give a flocculent crystal as the title compound. The data of mp, DSC graph, and X-ray powder diffraction pattern were same as those shown in Example 12.

Example 15

The Preparation of Maleate of Compound Z (Crystalline Form A)

The compound of Example 1 was dissolved in ethylene glycol dimethyl ether by heating, a small amount of water was added, and allowed to stand to precipitate a white needle crystal. The obtained precipitation was filtered off and dried to give the title compound. The data of mp, DSC graph, and X-ray powder diffraction pattern were same as those shown in Example 12.

Example 16

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (Crystalline Form A)

The compound of Example 1 was dissolved in isopropanol by heating, and allowed to stand to precipitate a white flocculent crystal. The obtained precipitation was filtered off and dried to give the title compound. The data of mp, DSC graph, and X-ray powder diffraction pattern were same to those shown in Example 12.

Example 17

The Preparation of Maleate of Compound Z (Crystalline Form A)

The compound of Example 1 was dissolved in acetonitrile by heating, and allowed to be cooled and stand to precipitate a white flocculent crystal. The obtained precipitation was filtered off and dried to give the title compound. The mp, DSC graph, and X-ray powder diffraction pattern were same as those shown in Example 12.

Example 18

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one maleate (Amorphous)

The compound of Example 1 was dissolved in dichloromethane, and petroleum ether was added dropwise until the solution is unclear. The solid precipitated under stirred, was filtered off and dried to give the title compound as a white solid. The X-ray powder diffraction pattern was shown in FIG. 3.

Example 19

The Preparation of Succinate of Compound Z (Crystalline Form I)

1.5 g of the compound of Example 2 was dissolved in 35 ml of acetone by heating, and allowed to stand to room temperature and gradually precipitate short needle crystals. The obtained precipitation was filtered off and dried to give the title compound. mp: 148.6-149.6° C., DSC graph thereof was shown in FIG. 4, and X-ray powder diffraction pattern was shown in FIG. 5.

Example 20

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one succinate (Crystalline Form I)

1.5 g of the compound of Example 2 was dissolved in 25 ml of acetonitrile by heating, and allowed to stand to room temperature and gradually precipitate short needle crystals. The obtained precipitation was filtered off and dried to give the title compound. The data of mp, DSC graph, and X-ray powder diffraction pattern were same as those shown in Example 19.

Example 21

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one succinate (Crystalline Form I)

The compound of Example 2 was dissolved in a mixed solvent of acetonitrile and water by heating, and allowed to stand to room temperature and gradually precipitate short needle crystals. The obtained precipitation was filtered off and dried to give the title compound. The data of mp, DSC graph, and X-ray powder diffraction pattern were same as those shown in Example 19.

Example 22

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one methanesulfonate (Crystalline Form I)

1.5 g of the compound of Example 3 was dissolved in 10 ml of acetonitrile, and allowed to stand overnight at room temperature and gradually precipitate needle crystals. The obtained precipitation was filtered off and dried to give the title compound. The mp was same as that in Example 3. The X-ray powder diffraction pattern was shown in FIG. 6.

Example 23

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one methanesulfonate (Crystalline Form I)

1.5 g of the compound of Example 3 was suspended in toluene, and heated under reflux and allowed to stand to room temperature. The obtained solid was filtered off and dried to give the title compound. The mp was same as that in Example 3. The X-ray powder diffraction pattern was shown in FIG. 6.

Example 24

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one methanesulfonate (Crystalline Form I)

1.5 g of the compound of Example 3 was dissolved in a mixed solvent of ethanol and water, heated at 60° C. for 1 hour, and allowed to stand to room temperature. The obtained solid was filtered off and dried to give the title compound. The mp was same as that in Example 3. The X-ray powder diffraction pattern was shown in FIG. 6.

Example 25

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form I)

1 g of the compound of Example 6 or 7 was dissolved in ethanol (8 ml) by heating, the mixture was naturally cooled to room temperature and gradually precipitated a white flocculent solid. The solid was filtered off and dried to give 0.51 g of the title compound as a white solid. mp: 193.2-194.8° C., DSC graph thereof was shown in FIG. 7, and X-ray powder diffraction pattern was shown in FIG. 8.

Example 26

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form I)

1 g of the compound of Example 6 or 7 was dissolved in isopropanol (15 ml) by heating, the mixture was naturally cooled to room temperature and gradually precipitated a white solid. The solid was filtered off and dried to give 0.62 g of the title compound as a white solid. The data of mp, DSC graph, and X-ray powder diffraction pattern were same as those shown in Example 25.

Example 27

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form II)

1 g of the compound of Example 6 or 7 was dissolved in acetone (35 ml), the mixture was heated under reflux, naturally cooled to room temperature and gradually precipitated a large flocculent white solid. The solid was filtered off and dried to give 0.71 g of the title compound as a white solid. mp: 187.1-188.0° C., DSC graph thereof was shown in FIG. 9, and X-ray powder diffraction pattern was shown in FIG. 10.

Example 28

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form II)

1 g of the compound of Example 6 or 7 was dissolved in acetonitrile (20 ml) and heated under reflux for 1 hour. The insoluble matter was filtered off, and the filtrate was naturally cooled to room temperature to precipitate flocculent solid. The resultant solid was filtered off and dried to give 0.32 g of the title compound as a white solid. The data of mp, DSC graph, and X-ray powder diffraction pattern were same as those shown in Example 27.

Example 29

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form II)

1 g of the compound of Example 6 or 7 was dissolved in N-methylpyrrolidone (5 ml) by heating. 40 ml of ethyl acetate was added to obtain a flocculent solid. The precipitated product was filtered off and dried to give 0.77 g of the title compound as a white solid. The data of mp, DSC graph, and X-ray powder diffraction pattern were same as those shown in Example 27.

Example 30

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form II)

1 g of the compound of Example 6 or 7 was dissolved in a mixed solvent of ethanol (5 ml) and ethylene glycol dimethyl ether (15 ml) by heating, and the mixture was cooled to room temperature, then a flocculent solid was gradually precipitated. The precipitated product was filtered off and dried to give 0.45 g of the title compound as a white solid. The data of mp, DSC graph, and X-ray powder diffraction pattern were same as those shown in Example 27.

Example 31

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form III)

1 g of the compound of Example 6 or 7 was dissolved in dichloromethane (5 ml), and petroleum ether (6 ml) was added dropwise to precipitate white solid. The precipitated product was filtered off and dried to give 0.89 g of the title compound as a white solid. mp: 176.6-178.1° C., DSC graph thereof was shown in FIG. 11, and X-ray powder diffraction pattern was shown in FIG. 12.

Example 32

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride (Crystalline Form IV)

0.5 g of the compound of Example 6 or 7 was suspended in toluene (30 ml), the suspension was heated under reflux for 1 hour, cooled to room temperature naturally, and allowed to stand. The resulting solid was filtered off and dried to give 0.46 g of the title compound as a white solid. mp: 183.8-189.2° C., DSC graph thereof was shown in FIG. 13, and X-ray powder diffraction pattern was shown in FIG. 14.

Example 33

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride monohydrate 1 g of the compound of Example 6 or 7 was suspended in 10 ml of ethanol and 0.5 ml of water, the suspension was heated at 60° C. for 1 hour, cooled to room temperature naturally, and allowed to stand overnight in a refrigerator so that the product gradually precipitated. The precipitated product was filtered off and dried at 55° C. to give 0.34 g of the title compound. TG spectrum: weight loss of 3.1% within 100° C.

Elemental analysis:

|  | C | H | N |
|---|---|---|---|
| Actual measured value | 52.25 | 6.71 | 14.68 |
| Theoretical value | 52.57 | 6.88 | 14.71 |

Example 34

The Preparation of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride dihydrate 1 g of the compound of Example 6 or 7 was dissolved in a mixed solvent of 6 ml of isopropanol and 0.6 ml of water by heating, the mixture was cooled to room temperature, and allowed to stand overnight in a refrigerator so that the product gradually precipitated. The precipitated product was filtered off and dried at 55° C. to give 0.2 g of the title compound.

Elemental analysis:

|  | C | H | N |
|---|---|---|---|
| Actual measured value | 51.23 | 6.67 | 14.43 |
| Theoretical value | 50.97 | 7.01 | 14.26 |

Example 35

Formulation Example

Capsule Preparations of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride

| Prescription | |
|---|---|
| Hydrochloride of compound Z | 20.0 g |
| Starch | 80.0 g |
| Lactose | 60.0 g |
| Microcrystalline cellulose | 35 g |
| 10% polyvinylpyrrolidone in ethanol | appropriate amount |
| Magnesium stearate | 0.5 g |

Total capsules: 1000

1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one hydrochloride and various accessories were screened by 80 mesh sieve, and weighed according to the prescription. Suitable particles were made with a 16-mesh sieve by using 10% polyvinylpyrrolidone in ethanol as a binder and dried at 65° C. The particles were granulated by using 14-mesh sieve, and magnesium stearate was added and mixed uniformly. The final product was obtained by loading the particles into capsules based on loading amount calculated by measuring the particles content.

Example 36

Formulation Example

Tablets of Compound Z Maleate

| Prescription | |
|---|---|
| Compound Z maleate | 20.0 g |
| Lactose | 120.0 g |
| Microcrystalline cellulose | 40.0 g |
| 8% of starch paste | appropriate amount |
| Sodium carboxymethyl starch | 10.0 g |
| Magnesium stearate | 1.0 g |

Total tablets: 1000

Compound Z maleate, microcrystalline cellulose, lactose, and sodium carboxymethyl starch were screened by 80 mesh sieve and mixed uniformly. The soft material was made by 8% starch paste. The particles were granulated by using 16 mesh sieve, dried and regulated. After that magnesium stearate was added and mixed uniformly. The final tablets were obtained by pressing based on the tablet weight calculated by measuring the particles content.

Experimental Examples

1. The Superiority of the Salts of the Compound Z (Compound Represented by Formula I)
(1) Comparison of the Stability of Compounds The basic compounds of compound Z and the maleate thereof were selected to compare the chemical stability through an impact factor test, and results were shown in Table 8:

TABLE 8

Stability test results of Compound Z and salts thereof

| | | Compound Z (basic) | | Maleate of Compound Z | |
|---|---|---|---|---|---|
| | | trait | purity | trait | purity |
| | 0 day | white | 98.25% | white | 99.79% |
| High temperature | 5 days | pale yellow | 94.70% | white | 99.69% |
| | 10 days | yellow | 94.55% | white | 99.76% |
| High humidity | 5 days | white | 98.02% | white | 99.79% |
| | 10 days | white | 98.20% | white | 99.80% |
| Light exposure | 5 days | pale yellow | 72.49% | white | 99.65% |
| | 10 days | pale yellow | 55.88% | white | 99.68% |

It can be seen from the comparison experiment results of the factors in the above table, the maleate of compound Z is stable under the conditions of high temperature, high humidity and light exposure. However, the compound Z (basic compound) is very unstable under light exposure condition, and the degradation is nearly 50% after 10 days, which illustrated that the basic compound Z has poor stability, is readily degradable, and has a poorer stability especially under lighting conditions. But the stability of salts thereof will increase greatly.

(2) Comparison on the Solubility of the Compounds

The basic compound Z and various salts of compound Z were selected to compare the solubility. Appropriate amount of sample was weighed, placed in glass tubes. The predetermined solvent was added gradually and the extension of clear of the solution was observed. The solvent included the follows: pure water (pH 6.2), hydrochloric acid solution (pH1.0), a standard potassium hydrogen phthalate buffer solution (pH 4.0), and a mixed phosphate buffer solution (pH 6.86).

TABLE 9

Comparison of solubilities of various salts of Compound Z

| | Solubility (mg/ml) | | | |
|---|---|---|---|---|
| | Pure water (pH 6.1) | hydrochloric acid solution (pH 1.0) | buffer solution (pH 6.86) | buffer solution (pH 4.0) |
| Compound Z (basic) | insoluble | >21 | insoluble | >5.88 |
| Maleate of compound Z | >11 | >42 | >19.8 | — |
| Succinate of compound Z | >40 | >56.5 | >49 | >41.3 |
| Methanesulfonate of compound Z | >24 | >153 | >115 | >45.5 |
| Citrate of compound Z | >17 | >125 | >83 | >59 |
| Hydrochlorid of compound Z | >11.5 | >106 | >153 | >150 |

It can be seen from the above table that the solubility of the basic compound Z in water and in other solvents is significantly less than those of salts of compound Z. Therefore, to transfer the compound Z into a form of salt is more advantage for a pharmaceutical preparation in human medicine use, since the water-solubility has a decisive influence on the preparation of pharmaceutical formulations, oral bioavailability etc.

(3) the Comparison of Appearance and Characters of the Compounds

The basic compound Z and various salts of compound Z were selected to compare the appearance and characters. The results were shown in the table below:

TABLE 10

The comparison of appearance and characters of the various salts of compound Z

| | Characters | Odor |
|---|---|---|
| Compound Z | white solid | pungent odor |
| Maleate of compound Z | white solid | no bad smell |
| hydrochloride of compound Z | white solid | no bad smell |
| Succinate of compound Z | white solid | no bad smell |
| Methanesulfonate of compound Z | white solid | no bad smell |
| Citrate of compound Z | white solid | no bad smell |

It can be seen from the above table that the salts of basic compound Z can mask the original pungent odor, so they are more suitable for oral administration.

(4) Comparison for the Efficacy of the Compound

The basic compound Z, maleate of compound Z and hydrochloride of compound Z were selected to perform the erectile dysfunction (ED) efficacy trials in vivo in rats according to the experimental method described in WO_2007056955_A1, so as to determine the increasing percentage of the rats cavernous body pressure/arterial blood pressure (ICP/BP) value after the administration. The results show that the efficacies of different compounds are similar to each other, and are similar to that of sildenafil or better.

TABLE 11 comparison of the efficacy of compound Z and various salts thereof

| compound | Dose (mg/kg) | n | ICP/BP increasing rate (%) |
|---|---|---|---|
| water | — | 5 | 5.63 ± 14.25 |
| Sildenafil | 10 | 5 | 73.10 ± 36.24** |
| Maleate of compound Z | 10 | 5 | 80.99 ± 17.01** |
| Hydrochloride of compound Z | 10 | 5 | 75.22 ± 14.43** |
| basic compound Z | 10 | 5 | 72.22 ± 19.28** | n represents the number of animals per group.

(5) Comparison of Pharmacokinetic Properties

The basic compound Z, maleate of compound Z, hydrochloride of compound Z, and succinate of compound Z were selected to perform the in vivo pharmacokinetic studies in rats, and results were shown in the accompanying FIGS. 15 and 16. The experimental results show that the in vivo pharmacokinetic properties in rats of the salts of compound Z are similar to or better than basic compound Z, especially the in vivo pharmacokinetic properties of hydrochloride of compound Z are superior to that of compound Z.

From the experimental results, it can be seen that the salt forms of the basic compound Z (compound represented by formula I) can greatly increase the stability of the compound, improve the water-solubility of the compound and mask unpleasant odor of the basic compound, while maintaining or improving the efficacy and pharmacokinetic properties of compound Z, therefore, they are more suitable for manufacturing the pharmaceutical preparations and being stored.

2. Superiority of Maleate of Compound Z, Crystalline Form A of Maleate of Compound Z With respect to various salts of compound Z, the present invention further compares the advantages and disadvantages of various salts. Based on the above study, a crystalline form A of maleate of compound Z was found to have a low moisture absorption and chemical stability. The crystalline form A of maleate of compound Z has overcome the defects of hydrochloride and methanesulfonate of the compound Z, i.e. they are highly hygroscopic, easily deliquescent and difficult to be stored, and is more suitable for applying in the pharmaceutical preparation.

(1) The Appearance, Composition of Compounds

The inventor studied on various crystalline forms of various salts of compound Z and compared the appearance, characters, components, crystalline form and extent of difficulty of manufacturing process. The results are shown in table below:

TABLE 12 comparison of compound Z and various crystalline forms thereof

| | items | | | | |
|---|---|---|---|---|---|
| sample | crystal water | static | stability | component | Crystalline form |
| Maleate of compound Z | no | no | stable | constant | Two types (crystalline form A, amorphous) |
| succinate of compound Z | no | no | stable | containing 1 to 2 succinic acid molecules | crystalline form I, amorphous |
| methanesulfonate of compound Z | no | no | stable | constant | crystalline form I, amorphous |
| citrate of compound Z | no | no | stable | — | — |
| Hydrochloride of compound Z | 0~2 | Some crystalline forms have electrostatic | Stable, but some crystalline forms are hygroscopic | With crystal water or absorbed water | Several types of crystal(crystalline form I, II, III, IV) |

It can be seen from the above table that the maleate of the compound Z is stable with constant composition and fewer crystalline forms. The crystalline form A is easy to be prepared and has good reproducibility. However, the hydrochloride of the compound Z has a variety of crystalline forms, strong hygroscopicity and intends to form solvates, especially hydrates, which will have some uncontrollable impacts on the determination of the components of the sample and quality control, and will negatively affect the subsequent preparation of pharmaceutical formulations.

(2) Comparison of the Hygroscopicity of Compound

The hygroscopicities of various salts of compound Z were studied. A certain amount of the sample was placed in a precisely-weighted glass weighing bottle with a stopper to accurately weight. Then the open glass weighing bottle was placed in a desiccator (the saturated potassium nitrate solution was placed at the lower part of the desiccator, the relative humidity was 92.5%) and stood for 48 hours at room temperature. And then the glass weighing bottle was covered with the stopper and weighted again. The absorbent weight can be calculated.

TABLE 13 comparison of hygroscopicities of various salts of compound Z

| | Moisture weight gain (%) |
|---|---|
| Basic compound Z | 0.39 |
| Maleate of compound Z | 1.56 |
| hydrochloride of compound Z | 6.46 |
| succinate of compound Z | 1.64 |
| methanesulfonate of compound Z | 31.05 |
| citrate of compound Z | 11.75 |

It can be seen from the above table that the maleate of the compound Z has the minimal hygroscopicity. However, the methanesulfonate of the compound Z has strong hygroscopicity, is easy to be deliquescent and form solvates, which will have some uncontrollable impacts on the determination of the components of the sample and will be negative to the pharmaceutical storage.

(4) The Efficacy of the Maleate of the Compound Z

The term of "maleate of the compound Z" herein refers to all various crystalline forms, mixed crystal, amorphousness, or solvates of the salts, including but not limited to crystalline form A.

1) in vitro activity and selectivity against various PDE isoenzyme

The in vitro activity and selectivity of maleate of the compound Z against various PDE isoenzyme were shown in the table below:

TABLE 14 activity and selectivity data of the maleate of compound Z against various PDE isoenzyme

| | Maleate of compound Z | | sildenafil | |
|---|---|---|---|---|
| PDEs | $IC_{50}$(nM) | $IC_{50}$(PDEs)/ $IC_{50}$(PDE5) | $IC_{50}$(nM) | $IC_{50}$(PDEs)/ $IC_{50}$(PDE5) |
| PDE1 | 462 | 203 | 460 | 88 |
| PDE2 | >100000 | >10000 | 6840 | 1310 |
| PDE3 | 22000 | 9649 | 7310 | 1400 |
| PDE4 | 4070 | 1785 | 5830 | 1117 |
| PDE5 | 2.28 | / | 5.22 | / |
| PDE6 | 45.2 | 20 | 42.2 | 8 |
| PDE7 | >100000 | >10000 | 46900 | 8985 |
| PDE8 | >100000 | >10000 | >100000 | >10000 |
| PDE9 | >100000 | >10000 | >100000 | >10000 |
| PDE10 | >100000 | >10000 | >100000 | >10000 |
| PDE11 | 6090 | 2671 | 4910 | 941 |

It can be seen from the above table that the compound has good in vitro activity and selectivity, and it is superior to sildenafil.

2) the treatment effect on pulmonary arterial hypertension (PAH) in rats

The effects of maleate of compound Z on pulmonary artery pressure of pulmonary arterial hypertension rats were studied according to the method described in the reference (J Pharmacol Sci, 111, 235-243 (2009)). The maleate of compound Z in each dose group can significantly reduce pulmonary arterial pressure in rats with pulmonary arterial hypertension, and each dose group has significant difference comparing with the model group and no significant difference comparing with the positive control group (FIG. 17, in which ΔΔP<0.01 compared with the normal control group; P<0.01 compared with the model group). It was shown in another set of experiments that a single intravenous administration of 1 mg/kg in rats can also significantly reduce mean pulmonary artery pressure and mean aortic pressure in rats with pulmonary arterial hypertension, and the maleate of the compound Z has a strong selectivity for the reduction of pulmonary artery pressure (FIG. 18, in which P<0.01 compared with the average aortic; ΔΔ P<0.01 compared with the saline group).

3) the effect on the cavernous pressure variation in rats and canidae due to the electric stimulus to the erectile nerve (in vivo efficacy against ED)

The effect of maleate of compound Z on the cavernous pressure variation in rats induced by the electric stimulus to the erectile nerve was studied according to the method described in the reference (International Journal of Impotence Research (2002) 14, 251-255).

After 2.50-5.00 mg/kg of maleate of the compound Z was administrated through rat duodenum, the ICP value (cavernous peak pressure) and ICP/BP values (cavernous peak pressure/carotid arterial blood pressure) in rat induced by the electric stimulus to the erectile nerve were significantly increased, which means a significant role in erectile function. This enhancement effect of maleate of the compound Z has similar potency to that of positive control sildenafil with the same dosage (FIG. 19).

The effect of maleate of the compound Z on the cavernous pressure in canidae induced by the electric stimulus to the erectile nerve was studied according to the method described in the reference (J Urol 1998 July; 160 (1): 242-6). After 3.75-15.00 mg/kg of maleate of the compound Z was administrated through canine duodenum, the ICP/BP value was measured, and the results shown that the compounds were effective (FIG. 20).

In summary, besides the above common advantages of the salts of the compound, the crystalline form A of maleate of compound Z still has the advantages of having a single and stable crystalline form, constant composition, no hygroscopicity, good synthetic process operability, stable characters, etc., and it is easy to be prepared and stored. It is the most preferable pharmaceutical preparation form in the pharmaceutical applications. Moreover, the maleate of compound Z has selective activity as a PDE5 inhibitor, and shows high activity and selectivity for PDE5 enzyme in the in vitro enzyme inhibitors screening test, and shows treatment efficacy to erectile dysfunction (ED) and pulmonary arterial hypertension (PAH) in vivo animal tests.

We claim:

1. A salt of 1-methyl-5-{2-propoxy-5-[[1-methyl-1-(2-pyrrolidin-1-yl)ethyl]aminosulfonyl]phenyl}-3-propyl-1,6-dihydro-7H-pyrazolo[4,3-D]pyrimidin-7-one represented by following formula (I) and pharmaceutically acceptable polymorph, solvate, hydrate, co-crystal, anhydride, or amorphous form thereof:

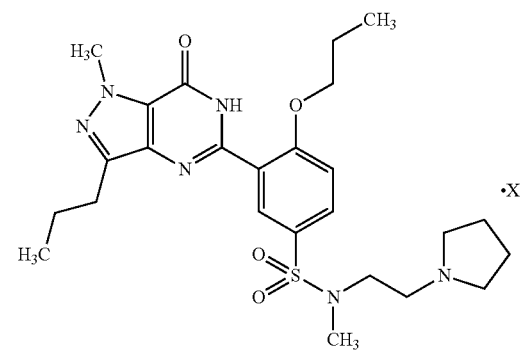

(I)

wherein, X represents maleic acid.

2. The compound represented by formula (I) according to claim 1, wherein the compound is crystalline form A, the crystalline form A has at least one X-ray diffraction peak at the diffraction angle 2θ selected from 6.30°±0.2°, 20.18°±0.2°, 22.30°±0.2° and 24.02°±0.2° Cu K-ALPHA1/ 40 KV/60 mA using a rotating target polycrystalline diffraction instrument.

3. The compound represented by formula (I) according to claim 2, wherein the compound is crystalline form A, the crystalline form A has an X-ray powder diffraction pattern as shown in FIG. 2 under Cu K-ALPHA1/40 KV/60 mA using a rotating target polycrystalline diffraction instrument.

4. The compound represented by formula (I) according to claim 1, wherein the compound is amorphous, the amorphous compound has an X-ray powder diffraction pattern as shown in FIG. 3 under Cu K-ALPHA1/40 KV/60 mA using a rotating target polycrystalline diffraction instrument.

* * * * *

UNITED STATES PATENT AND TRADEMARK OFFICE
CERTIFICATE OF CORRECTION

PATENT NO. : 9,527,849 B2  
APPLICATION NO. : 14/238790  
DATED : December 27, 2016  
INVENTOR(S) : Jianfeng Li et al.

Page 1 of 1

It is certified that error appears in the above-identified patent and that said Letters Patent is hereby corrected as shown below:

On the Title Page

Column 1, item (73) Assignees, after "SHANGHAI INSTITUTE OF MATERIA MEDICA, CHINESE ACADEMY OF SCIENCES" insert --, Shanghai (CN);--.

Column 1, item (73) Assignees, after "TOPHARMAN SHANDONG CO., LTD.," delete "Shanghai" and insert --Shandong--.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*